US011605018B2

(12) United States Patent
Agassi et al.

(10) Patent No.: US 11,605,018 B2
(45) Date of Patent: Mar. 14, 2023

(54) ONTOLOGY-GUIDED RECONCILIATION OF ELECTRONIC RECORDS

(71) Applicant: CERNER INNOVATION, INC., Kansas City, KS (US)

(72) Inventors: Natalee Agassi, Blue Bell, PA (US); Emin Agassi, Blue Bell, PA (US)

(73) Assignee: Cerner Innovation, Inc., Kansas City, MO (US)

( * ) Notice: Subject to any disclaimer, the term of this patent is extended or adjusted under 35 U.S.C. 154(b) by 1056 days.

(21) Appl. No.: 16/233,341

(22) Filed: Dec. 27, 2018

(65) Prior Publication Data

US 2019/0197421 A1   Jun. 27, 2019

Related U.S. Application Data

(60) Provisional application No. 62/610,714, filed on Dec. 27, 2017.

(51) Int. Cl.
*G06N 20/00* (2019.01)
*G06N 5/046* (2023.01)
(Continued)

(52) U.S. Cl.
CPC ............. *G06N 20/00* (2019.01); *G06N 5/046* (2013.01); *G16H 10/60* (2018.01); *G16H 50/50* (2018.01); *G16H 70/40* (2018.01); *G16H 70/60* (2018.01)

(58) Field of Classification Search
CPC ........ G06N 20/00; G06N 5/046; G06N 5/022; G06N 5/025; G06N 5/045; G16H 10/60; G16H 50/50; G16H 70/40; G16H 70/60
See application file for complete search history.

(56) References Cited

U.S. PATENT DOCUMENTS

| 4,847,764 A | 7/1989 | Halvorson |
| 5,072,383 A | 12/1991 | Brimm et al. |

(Continued)

FOREIGN PATENT DOCUMENTS

| EP | 0090971 A1 | 10/1983 |
| EP | 0950971 A2 | 10/1999 |

(Continued)

OTHER PUBLICATIONS

"Apelon Products", Product Overviews, Retrieved from Internet URL:<http://apelon.com/products/products.htm> on May 22, 2002, 45 pages.

(Continued)

*Primary Examiner* — Pei Yong Weng
(74) *Attorney, Agent, or Firm* — Invoke

(57) ABSTRACT

Methods, systems, and computer-readable media are disclosed herein that employ a contextually intelligent framework. In accordance with embodiments, a knowledge model having rules, axioms, and a domain ontology is evaluated to determine rules that are redundant to other rules and axioms, to determines those rules thresholds that may be refactored to generate composite rules and reduce the overall quantity of rules in the knowledge model, and to generate and add new concepts as axioms to the domain ontology as determined through refactoring. Methods, systems, and computer-readable media are disclosed herein that use the refactored and improved knowledge model to reconcile information currently stored in one system with information imported from a plurality of diverse systems, in order to generate recommendations that promote continuity of care in clinical settings.

11 Claims, 16 Drawing Sheets

(51) Int. Cl.

| | |
|---|---|
| *G16H 70/40* | (2018.01) |
| *G16H 70/60* | (2018.01) |
| *G16H 50/50* | (2018.01) |
| *G16H 10/60* | (2018.01) |

(56) References Cited

U.S. PATENT DOCUMENTS

| | | |
|---|---|---|
| 5,077,666 A | 12/1991 | Brimm et al. |
| 5,530,861 A | 6/1996 | Diamant et al. |
| 5,692,125 A | 11/1997 | Schloss et al. |
| 5,721,913 A | 2/1998 | Ackroff et al. |
| 5,745,901 A | 4/1998 | Entner et al. |
| 5,758,095 A | 5/1998 | Albaum et al. |
| 5,784,635 A | 7/1998 | McCallum |
| 5,790,119 A | 8/1998 | Sklut et al. |
| 5,799,297 A | 8/1998 | Goodridge et al. |
| 5,826,239 A | 10/1998 | Du et al. |
| 5,832,455 A | 11/1998 | Hayashi et al. |
| 5,842,173 A | 11/1998 | Strum et al. |
| 5,842,976 A | 12/1998 | Williamson |
| 5,911,687 A | 6/1999 | Sato et al. |
| 5,923,018 A | 7/1999 | Kameda et al. |
| 5,937,388 A | 8/1999 | Davis et al. |
| 5,970,463 A | 10/1999 | Cave et al. |
| 5,987,422 A | 11/1999 | Buzsaki |
| 5,991,728 A | 11/1999 | DeBusk et al. |
| 6,014,629 A | 1/2000 | Debruin-Ashton |
| 6,037,940 A | 3/2000 | Schroeder et al. |
| 6,052,669 A | 4/2000 | Smith et al. |
| 6,052,684 A | 4/2000 | Du |
| 6,061,506 A | 5/2000 | Wollaston et al. |
| 6,064,984 A | 5/2000 | Ferguson et al. |
| 6,067,548 A | 5/2000 | Cheng |
| 6,072,493 A | 6/2000 | Driskell et al. |
| 6,078,982 A | 6/2000 | Du et al. |
| 6,085,184 A | 7/2000 | Bertrand et al. |
| 6,088,679 A | 7/2000 | Barkley |
| 6,115,646 A | 9/2000 | Fiszman et al. |
| 6,151,583 A | 11/2000 | Ohmura et al. |
| 6,208,345 B1 | 3/2001 | Sheard et al. |
| 6,208,974 B1 | 3/2001 | Campbell et al. |
| 6,223,164 B1 | 4/2001 | Seare et al. |
| 6,225,998 B1 | 5/2001 | Okita et al. |
| 6,278,901 B1 | 8/2001 | Winner et al. |
| 6,279,009 B1 | 8/2001 | Smirnov et al. |
| 6,304,886 B1 | 10/2001 | Bernardo et al. |
| 6,308,163 B1 | 10/2001 | Du et al. |
| 6,308,188 B1 | 10/2001 | Bernardo et al. |
| 6,311,192 B1 | 10/2001 | Rosenthal et al. |
| 6,314,556 B1 | 11/2001 | DeBusk et al. |
| 6,347,329 B1 | 2/2002 | Evans |
| 6,349,329 B1 | 2/2002 | Mackintosh et al. |
| 6,430,538 B1 | 8/2002 | Bacon et al. |
| 6,458,080 B1 | 10/2002 | Brown et al. |
| 6,484,144 B2 | 11/2002 | Martin et al. |
| 6,697,784 B2 | 2/2004 | Bacon et al. |
| 6,728,947 B1 | 4/2004 | Bengston |
| 6,912,549 B2 | 6/2005 | Rotter et al. |
| 6,915,265 B1 | 7/2005 | Johnson |
| 6,966,049 B2 | 11/2005 | Lepejian et al. |
| 6,970,844 B1 | 11/2005 | Bierenbaum |
| 6,978,268 B2 | 12/2005 | Thomas et al. |
| 7,027,997 B1 | 4/2006 | Robinson et al. |
| 7,035,862 B2 | 4/2006 | Patitucci |
| 7,047,535 B2 | 5/2006 | Lee et al. |
| 7,051,012 B2 | 5/2006 | Cole et al. |
| 7,136,824 B2 | 11/2006 | Masuda et al. |
| 7,181,375 B2 | 2/2007 | Rao et al. |
| 7,184,967 B1 | 2/2007 | Mital et al. |
| 7,240,324 B2 | 7/2007 | Casati et al. |
| 7,275,039 B2 | 9/2007 | Setteducati |
| 7,296,056 B2 | 11/2007 | Yaung |
| 7,318,059 B2 | 1/2008 | Thomas et al. |
| 7,403,936 B2 | 7/2008 | Rao et al. |
| 7,428,495 B2 | 9/2008 | Dhar et al. |
| 7,437,302 B2 | 10/2008 | Haskell et al. |
| 7,447,644 B2 | 11/2008 | Brandt et al. |
| 7,457,731 B2 | 11/2008 | Rao |
| 7,457,765 B2 | 11/2008 | Thompson et al. |
| 7,590,932 B2 | 9/2009 | Britton et al. |
| 7,617,078 B2 | 11/2009 | Rao et al. |
| 7,630,947 B2 | 12/2009 | Pandya et al. |
| 7,653,566 B2 | 1/2010 | Kim et al. |
| 7,689,441 B1 | 3/2010 | Craft |
| 7,711,404 B2 | 5/2010 | Rao et al. |
| 7,725,330 B2 | 5/2010 | Rao et al. |
| 7,744,540 B2 | 6/2010 | Rao et al. |
| 7,756,728 B2 | 7/2010 | Maughan et al. |
| 7,805,385 B2 | 9/2010 | Steck et al. |
| 7,840,511 B2 | 11/2010 | Rosales et al. |
| 7,844,560 B2 | 11/2010 | Krishnan et al. |
| 7,877,272 B2 | 1/2011 | Rosales et al. |
| 7,890,349 B2 | 2/2011 | Cole et al. |
| 7,895,055 B2 | 2/2011 | Schneider et al. |
| 7,917,377 B2 | 3/2011 | Rao et al. |
| 7,937,655 B2 | 5/2011 | Teng et al. |
| 3,000,978 A1 | 8/2011 | Wager et al. |
| 8,027,849 B2 | 9/2011 | Johnson et al. |
| 8,046,362 B2 | 10/2011 | Bayliss |
| 8,200,527 B1 | 6/2012 | Thompson et al. |
| 8,214,224 B2 | 7/2012 | Rao et al. |
| 8,214,225 B2 | 7/2012 | Rao et al. |
| 8,219,416 B2 | 7/2012 | Auker et al. |
| 8,280,750 B2 | 10/2012 | Krishnan et al. |
| 8,326,667 B2 | 12/2012 | Johnson |
| 8,392,152 B2 | 3/2013 | Rao |
| 8,392,232 B2 | 3/2013 | McGillin |
| 8,571,884 B2 | 10/2013 | Badgett et al. |
| 8,579,784 B2 | 11/2013 | Krishnan et al. |
| 8,768,741 B1 | 7/2014 | Hinton et al. |
| 8,775,207 B2 | 7/2014 | Abraham et al. |
| 9,336,283 B2 | 5/2016 | Giang et al. |
| 9,639,662 B2 | 5/2017 | Sethumadhavan et al. |
| 9,703,927 B2 | 7/2017 | Chaudhri et al. |
| 9,824,316 B2 | 11/2017 | Junker et al. |
| 2001/0001144 A1 | 5/2001 | Kapp |
| 2001/0032108 A1 | 10/2001 | Sieron et al. |
| 2001/0037227 A1 | 11/2001 | Mcinnis et al. |
| 2002/0018066 A1 | 2/2002 | Vizer |
| 2002/0059201 A1 | 5/2002 | Work |
| 2002/0059251 A1 | 5/2002 | Stern et al. |
| 2002/0065701 A1 | 5/2002 | Kim et al. |
| 2002/0128871 A1 | 9/2002 | Adamson et al. |
| 2002/0128890 A1 | 9/2002 | Dick et al. |
| 2002/0129031 A1 | 9/2002 | Lau et al. |
| 2002/0170035 A1 | 11/2002 | Casati et al. |
| 2003/0023593 A1 | 1/2003 | Schmidt |
| 2003/0023728 A1 | 1/2003 | Yaung |
| 2003/0045958 A1 | 3/2003 | Brandt et al. |
| 2003/0050800 A1 | 3/2003 | Brandt et al. |
| 2003/0074225 A1 | 4/2003 | Borsand et al. |
| 2003/0078813 A1 | 4/2003 | Haskell et al. |
| 2003/0149714 A1 | 8/2003 | Casati et al. |
| 2003/0158832 A1 | 8/2003 | Sijacic et al. |
| 2004/0015841 A1 | 1/2004 | Lepejian et al. |
| 2005/0027566 A1 | 2/2005 | Haskell |
| 2006/0184475 A1* | 8/2006 | Krishnan ............... G16H 50/20 706/20 |
| 2006/0184943 A1 | 8/2006 | Delmonego et al. |
| 2007/0130206 A1* | 6/2007 | Zhou ..................... G16H 10/60 |
| 2009/0043634 A1 | 2/2009 | Tisdale |
| 2009/0089092 A1 | 4/2009 | Johnson et al. |
| 2010/0004948 A1 | 1/2010 | Toomey et al. |
| 2010/0131289 A1 | 5/2010 | Brandt et al. |
| 2011/0071850 A1 | 3/2011 | Nuthi |
| 2011/0320187 A1* | 12/2011 | Motik ................. G06F 16/3344 704/9 |
| 2012/0041910 A1 | 2/2012 | Ludik et al. |
| 2012/0239671 A1 | 9/2012 | Chaudhri et al. |
| 2012/0245948 A1 | 9/2012 | Nolte et al. |
| 2012/0253836 A1 | 10/2012 | Nolte et al. |
| 2013/0046558 A1 | 2/2013 | Landi et al. |
| 2013/0085977 A1 | 4/2013 | Junker |
| 2013/0204830 A1 | 8/2013 | Franke |

(56) References Cited

U.S. PATENT DOCUMENTS

| | | | |
|---|---|---|---|
| 2014/0058748 | A1 | 2/2014 | Ford et al. |
| 2014/0095203 | A1 | 4/2014 | Anand et al. |
| 2014/0244300 | A1 | 8/2014 | Bess et al. |
| 2015/0081326 | A1 | 3/2015 | Krishnapuram et al. |
| 2015/0120327 | A1 | 4/2015 | Compton et al. |
| 2015/0149362 | A1* | 5/2015 | Baum .................. G06F 21/602 705/51 |
| 2015/0317311 | A1 | 11/2015 | Cannon et al. |
| 2016/0350361 | A1 | 12/2016 | Chen et al. |
| 2017/0109477 | A1 | 4/2017 | Farooq et al. |
| 2017/0124269 | A1 | 5/2017 | Mcnair et al. |
| 2017/0161439 | A1 | 6/2017 | Raduchel et al. |
| 2017/0212748 | A1 | 7/2017 | Agnew et al. |
| 2018/0181644 | A1 | 6/2018 | Lyons et al. |
| 2019/0303371 | A1 | 10/2019 | Rowe et al. |
| 2020/0342991 | A1 | 10/2020 | Hu et al. |
| 2021/0182306 | A1 | 6/2021 | Agassi et al. |

FOREIGN PATENT DOCUMENTS

| | | |
|---|---|---|
| EP | 1065618 A2 | 1/2001 |
| EP | 1304645 A2 | 4/2003 |
| JP | 2001-202408 A | 7/2001 |
| WO | 99/24927 A1 | 5/1999 |
| WO | 00/03344 A1 | 1/2000 |
| WO | 00/14618 A2 | 3/2000 |
| WO | 00/33238 A3 | 11/2000 |
| WO | 2017/188987 A2 | 11/2017 |

OTHER PUBLICATIONS

Batch, Kim, "Who Needs a Standard Medical Terminology", Enterprise Architect Center for Biomedical Information, University of Pittsburgh, 9 pages.

Bechhofer et al., "Terminologies and Terminology Servers for Information Environments", Proceedings of Eighth IEEE International Workshop on Software Technology and Engineering Practice Incorporating Computer Aided Software Engineering, 1997, pp. 484-497.

Bertino et al., "A Flexible Model Supporting the Specification and Enforcement of Role-Based Authorization in Workflow Management Systems.", Proceedings of the Second ACM Workshop on Role-Based Access Control, 1997, pp. 1-12.

Chun et al., "Dynamic Composition of Workflows for Customized eGovernment Service Delivery", Proceedings of the 2002 Annual National Conference on Digital Government Research, 2002, 7 pages.

Dewan et al., "Workflow Optimization Through Task Redesign in Business Information Processes", Proceedings of the Thirty-First Hawaii International Conference on System Sciences, vol. 1, 1998, 13 pages.

Elkin et al., "Automated Enhancement of Description Logic-Defined Terminologies to Facilitate Mapping to ICD9-CM", Journal of Biomedical Informatics Academic, vol. 35, 2002, pp. 281-288.

Georgakopoulos et al., "An Overview of Workflow Management: From Process Modeling to Workflow Automation Infrstructure", Distributed and Parallel Databases, vol. 3, 1995, pp. 119-153.

Healthcare Informatics: Feb. 1999 News and Trends, Retrieved from: <http://www.healthcare-informatics.com/issues/1999/02_99/news.htm> on May 22, 2002. 12 pages.

"Health Supplier", Retrieved from internet URL:<http://www.healthtrade.com.tw/en/left/healthsupplier-en.htm>, 2000, 4 pages.

Hogarth et al., "Terminology Query Language: A Server Interface For Concept-Oriented Terminology Systems", Proceedings of the AMIA Symposium, 2000, 5 pages.

Horrocks, Ian, "Description Logic: Axioms and Rules", Dagstuhl Rule Markup Techniques, Feb. 7, 2002, pp. 1-51.

Ingenerf et al., "Standardized Terminological Services Enabling Semantic Interoperability Between Distributed and Heterogeneous Systems", International Journal of Medicine Informatics, vol. 64, 2001, pp. 223-240.

Lowe et al., "The Image Engine HPCC Project. A Medical Digital Library System Using Agent-Based Technology to Create an Integrated View of the Electronic Medical Record.", Proceedings of the Third Forum on Research and Technology Advances in Digital Libraries, 1996, pp. 45-56.

Marazakis et al., "Management of Work Sessions in Dynamic Open Environments", Proceedings of International Workshop on Workflow Management, 1998, 6 pages.

Nielsen et al., "Using Domino Workflow", IBM Corporation, International Technical Support Organization, 2000, 31 pages.

Nikolai et al., "Thesaurus Federations: A Framework for the Flexible Integration of Heterogeneous, Autonomous Thesauri", Proceedings IEEE International Forum on Research and Technology Advances in Digital Libraries, Apr. 22-24, 1998, pp. 46-55.

Noy, et al., "Ontology Development 101: A Guide to Creating Your First Ontology", Web Page <https://protege.stanford.edu/publications/ontology_development/ontology101.pdf>, Jul. 23, 2001, retrieved from Internet Archive Wayback Machine <https://web.archive.org/web/20010801000000*/https://protege.stanford.edu/publications/ontology_development/ontology101.pdf> on Dec. 19, 2018, pp. 1-20.

"OWL, An ontology Language", Ontogenesis, Jan. 21, 2010, pp. 1-6.

"Organization Profile (OP FORM)", Retrieved from the internet URL: <http://www.unece.org/ceiproj/ex1op.htm>. on Jun. 7, 2002, 3 pages.

Raths, David, "The Importance of Bringing EMS Systems Into the HIE Loop", Healthcare Informatics, Health It Summit Series, May 31, 2017, 3 pages.

Rector et al., "A Terminology Server for Medical Language and Medical Information Systems", Method of Information in Medicine, vol. 34, No. 1/2, 1995, pp. 147-157.

"Signature Product Description Information", Jun. 1985, 4 pages.

Yu et al., "Representing Genomic Knowledge in the UMLS Semantic Network", Proceedings of AMIA Annual Symposium, 1999, pp. 181-185.

Zhao et al., "Temporal Workflow Management in a Claim Handling System", Proceedings of the International Joint Conference on Work Activities Coordination and Collaboration, 1999, pp. 187-195.

Pre-Interview First Office action received for U.S. Appl. No. 16/233,348, dated Apr. 7, 2021, 4 pages.

"Towards Refactoring of Rule-based, in-place Model Transformation Systems", Available online at: <https://dl.acm.org/doi/10.1145/2432497.2432506>, 2021, pp. 41-46.

Non-Final Office Action received for U.S. Appl. No. 16/715,640, dated Jun. 9, 2022, 30 pages.

Final Office Action received for U.S. Appl. No. 16/233,348, dated Dec. 24, 2021, 52 pages.

Final Office Action received for U.S. Appl. No. 16/715,640, dated Dec. 10, 2021, 25 pages.

Non-Final Office Action received for U.S. Appl. No. 16/715,640, dated Aug. 26, 2021, 23 pages.

Non-Final Office Action received for U.S. Appl. No. 16/233,348, dated Oct. 26, 2022, 27 pages.

\* cited by examiner

☐ [(systolic blood pressure cuff/(-,100.0)), (Age from 0 day), (Age up to 1 month)), => (Systolic blood pressure cuff result observable[[is judged as VALUE decreased]])]
☐ [(systolic blood pressure cuff/(-,65.0)), (Age from 1 month), (Age up to 1 week)), => (Systolic blood pressure cuff result observable[[is judged as VALUE decreased]])]
☐ [(systolic blood pressure cuff/(-,75.0)), (Age from 1 week), (Age up to 1 month)), => (Systolic blood pressure cuff result observable[[is judged as VALUE decreased]])]
☐ [(systolic blood pressure cuff/(-,90.0)), (Age from 12 years), (Age up to 18 years)), => (Systolic blood pressure cuff result observable[[is judged as VALUE decreased]])]
☐ [(systolic blood pressure cuff/(-,90.0)), (Age from 18 years)), => (Systolic blood pressure cuff result observable[[is judged as VALUE decreased]])]
☐ [(systolic blood pressure cuff/(-,90.0)), (Age from 2 years), (Age up to 5 years)), => (Systolic blood pressure cuff result observable[[is judged as VALUE decreased]])]
☐ [(systolic blood pressure cuff/(-,94.0)), (Age from 5 years), (Age up to 12 years)), => (Systolic blood pressure cuff result observable[[is judged as VALUE decreased]])]
☐ [(systolic blood pressure cuff/(-,94.0)), => (Systolic blood pressure cuff result observable[[is judged as VALUE decreased]])]
☐ [(systolic blood pressure invasive/(-,100.0)), (Age from 1 month), (Age up to 2 years), => (Systolic blood pressure invasive result observable[[is judged as VALUE decreased]])]
☐ [(systolic blood pressure invasive/(-,65.0)), (Age from 0 day), (Age up to 1 week), => (Systolic blood pressure invasive result observable[[is judged as VALUE decreased]])]
☐ [(systolic blood pressure invasive/(-,75.0)), (Age from 1 week), (Age up to 1 month), => (Systolic blood pressure invasive result observable[[is judged as VALUE decreased]])]
☐ [(systolic blood pressure invasive/(-,90.0)), (Age from 12 years), (Age up to 18 years), => (Systolic blood pressure invasive result observable[[is judged as VALUE decreased]])]
☐ [(systolic blood pressure invasive/(-,90.0)), (Age from 18 years), => (Systolic blood pressure invasive result observable[[is judged as VALUE decreased]])]
☐ [(systolic blood pressure invasive/(-,90.0)), (Age from 2 years), (Age up to 5 years), => (Systolic blood pressure invasive result observable[[is judged as VALUE decreased]])]
☐ [(systolic blood pressure invasive/(-,94.0)), (Age from 5 years), (Age up to 12 years), => (Systolic blood pressure invasive result observable[[is judged as VALUE decreased]])]
☐ [(systolic blood pressure invasive/(-,94.0)), => (Systolic blood pressure invasive result observable[[is judged as VALUE decreased]])]
☐ [(temperature degrees/(-,36.0)), (Age from 0 day), (Age up to 1 week), => (Body temperature observable[[is judged as VALUE decreased]])]
☐ [(temperature degrees/(-,36.0)), (Age from 1 month), (Age up to 2 years), => (Body temperature observable[[is judged as VALUE decreased]])]
☐ [(temperature degrees/(-,36.0)), (Age from 1 week), (Age up to 1 month), => (Body temperature observable[[is judged as VALUE decreased]])]
☐ [(temperature degrees/(-,36.0)), (Age from 12 years), (Age up to 18 years), => (Body temperature observable[[is judged as VALUE decreased]])]
☐ [(temperature degrees/(-,36.0)), (Age from 18 years), => (Body temperature observable[[is judged as VALUE decreased]])]
☐ [(temperature degrees/(-,36.0)), (Age from 2 years), (Age up to 5 years), => (Body temperature observable[[is judged as VALUE decreased]])]
☐ [(temperature degrees/(-,36.0)), (Age from 5 years), (Age up to 12 years), => (Body temperature observable[[is judged as VALUE decreased]])]
☐ [(temperature degrees/(-,36.0)), => (Body temperature observable[[is judged as VALUE decreased]])]

*FIG. 2.*

Rules

Show [5 ▼] entries             Search: [ ]

| Comparison | Model 1 | Model 2 | Rules in 1 | Rules in 2 | Rules in 1, not in 2 | Rules in 2, not in 1 |
|---|---|---|---|---|---|---|
| sepsis1-v sepsis1-fca | sepsis1 | sepsis1-fca | 154 | 73 | 141 | 60 |

| Comparison | Model 1 | Model 2 | Rules in 1 | Rules in 2 | Rules in 1, not | Rules in 2, not |

Ontology

Show [5 ▼] entries             Search: [ ]

| Comparison | Model 1 | Model 2 | Axioms 1 | Axioms 2 | Axioms in 1, not in 2 | Axioms in 2, not in 1 | Domain concepts in 1, not in 2 | Domain concepts in 2, not in 1 |
|---|---|---|---|---|---|---|---|---|
| sepsis1-v sepsis1-fca | sepsis1 | sepsis1-fca | 838 | 933 | 0 | 95 | 0 | 28 |

| Comparison | Model 1 | Model 2 | Axioms 1 | Axioms 2 | Axioms in | Axioms in | Domain conc | Domain conc |

*FIG. 7.*

Distribution of Rule Size

Show [100] entries    Search: [    ]

| Comparison | Metric | Mean.1 | Mean.2 | Median.1 | Median.2 | SD.1 | SD.2 |
|---|---|---|---|---|---|---|---|
| sepsis1-v sepsis1-fca | Premise size | 2.5921053 | 1.7323944 | 3.0000000 | 2.0000000 | 0.7127529 | 0.4768272 |
| sepsis1-v sepsis1-fca | Consequence size | 1.0657895 | 1.0140845 | 1.0000000 | 1.0000000 | 0.2487333 | 0.1186782 |
| sepsis1-v sepsis1-fca | Rule size | 3.6578947 | 2.7464789 | 4.0000000 | 3.0000000 | 0.6314628 | 0.4990937 |
| sepsis1-v sepsis1-fca | Specific value premis nodes count | 0.9013158 | 0.8309859 | 1.0000000 | 1.0000000 | 0.2992235 | 0.3774318 |
| sepsis1-v sepsis1-fca | Referenced domain references count | 4.6118421 | 3.4929577 | 5.0000000 | 4.0000000 | 1.0424712 | 1.1067745 |
| sepsis1-v | Reference entity | 2.5065789 | 2.0704225 | 3.0000000 | 3.0000000 | 1.1157910 | 1.3971803 |

ONTOLOGY-GUIDED RECONCILIATION OF ELECTRONIC RECORDS

CROSS REFERENCE

This application entitled "Ontology-Guided Reconciliation of Electronic Records," is a non-provisional application that claims the benefit of provisional U.S. App. No. 62/610,714, filed on 27 Dec. 2017 and entitled "Ontology-Guided Reconciliation of Electronic Records," the entirety of which is incorporated herein by reference.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

In brief and at a high level, this disclosure describes, among other things, methods, systems, and computer-readable media for improving the structure of a knowledge model and improving the knowledge of a domain ontology.

In one embodiment, a method is provided. The method determines that two or more rules in a knowledge model have different thresholds and correspond to a matching path. In embodiments, the method comprises generating a replacement rule having a composite threshold by refactoring the different thresholds of the two or more rules. Then, in some embodiments, the method modifies the knowledge model by replacing the two or more rules with the replacement rule.

In another embodiment, one or more computer-readable storage media are provided for storing computer instructions thereon for execution by one or more processors to perform a method. The method receives a knowledge model comprising a plurality of rules. The method, in some embodiments, determines a total number of different forms capable of being generated from the plurality of rules. For at least one form in the plurality of forms, the method determines that at least two of the plurality of rules correspond to the at least one form. The method further determines that at least two of the plurality of rules that correspond to the at least one form have different thresholds. Continuing, in an embodiment, the method determines that the at least two of the plurality of rules having different thresholds correspond to a matching path in the at least one form. In embodiments, the method generates a replacement rule having a composite threshold by refactoring the different thresholds of the at least two of the plurality of rules. The method then modifies the knowledge model by replacing the at least two of the plurality of rules with the replacement rule.

In brief and at a high level, this disclosure also describes, among other things, methods, systems, and computer-readable media for applying concept- or ontology-based models, also known as ontology-based models, to reconcile the information currently stored in one system with information imported from a plurality of diverse systems.

In one embodiment, a computerized method is provided in an embodiment of the present invention. The computerized method obtains electronic records from a plurality of diverse systems. In embodiments, the plurality of diverse record systems having the electronic records maintain the records in different data formats. The method reconciles the electronic records obtained from the plurality of diverse systems with one another using an ontology-based model. Based on reconciling the electronic records, the method generates inferential knowledge.

A system is provided in another embodiment. The system comprises a processor and a memory coupled to the processor. The system further comprise a module stored in the memory and executed via the processor. The module obtains electronic records from a plurality of diverse systems, in embodiments. The plurality of diverse record systems stored the electronic records in different data formats, in some embodiments. The module reconciles the electronic records obtained from the plurality of diverse systems with one another using an ontology-based model, in accordance with the system. In embodiments, the module generates inferential knowledge based on reconciling the electronic records.

In yet another embodiment, a method is provided. The method obtains electronic records from a plurality of diverse system having electronic records in different data formats, in embodiments. The method reconciles the electronic records obtained from the plurality of diverse systems with one another using an ontology-based model in a knowledge model. In reconciliation, the method applies one or more of the medications ontology model, the allergies ontology model, the immunizations ontology model, and the problems ontology model to the electronic records, in an embodiment. Additionally, in reconciling the a the electronic records, the method recognizes discrete data items that are relevant to a meaningful use decision regarding one or more of medications, allergies, immunizations, and problems. In embodiments, the method generates inferential knowledge based on the discrete data items recognized as being relevant to a meaningful use decision regarding one or more of medications, allergies, immunizations, and problems, by applying a forecasting model to the discrete data items, the forecasting model being specific to one of medications, allergies, immunizations, or problems.

In an embodiment, another method is provided. In such an embodiment, the method obtains electronic records from a plurality of diverse systems, the plurality of diverse record systems having the electronic records in different data formats. The method reconciles the electronic records obtained from the plurality of diverse systems with one another using an ontology-based model. In order to reconcile the electronic records, the method identifies, in the electronic records obtained from the plurality of diverse systems, information related to one or more of a medications ontology model, an allergies ontology model, an immunizations ontology model, and a problems ontology model. Further, the method applies one or more of the medications ontology model, the allergies ontology model, the immunizations ontology model, and the problems ontology model to the electronic records obtained from the plurality of diverse systems. Then, based on the application of one or more of the medications ontology model, the allergies ontology model, the immunizations ontology model, and the problems ontology model to the electronic records, the method recognizes discrete data items that are relevant to a meaningful use decision regarding one or more of medications, allergies, immunizations, and problems. The method continues by generating inferential knowledge based on the discrete data items recognized as being relevant to a meaningful use decision regarding one or more of medications, allergies, immunizations, and problems. In embodiment, the method generates inferential knowledge by applying a forecasting model to the discrete data items, the forecasting model being specific to one of medications, allergies, immunizations, or problems. Based on applying the forecasting model to the discrete data items, the method generates a recommendation specific to one of medications, allergies, immunizations, or problems, wherein the recommendation requests a user input to confirm.

BRIEF DESCRIPTION OF DRAWINGS

Illustrative embodiments of the present invention are described in detail below with reference to the attached drawing figures, and wherein:

FIG. 2 depicts a simplified representation of exemplary rules in accordance with an embodiment of the present invention;

FIG. 7 depicts an exemplary model structure metrics report in accordance with an embodiment of the present invention;

FIG. 8 depicts an exemplary model structure metrics report in accordance with an embodiment of the present invention;

FIG. 14 depicts an exemplary graphical user interface (GUI) in accordance with an embodiment of the present invention;

FIG. 15 depicts an exemplary graphical user interface (GUI) in accordance with an embodiment of the present invention.

DETAILED DESCRIPTION

Figure 1:
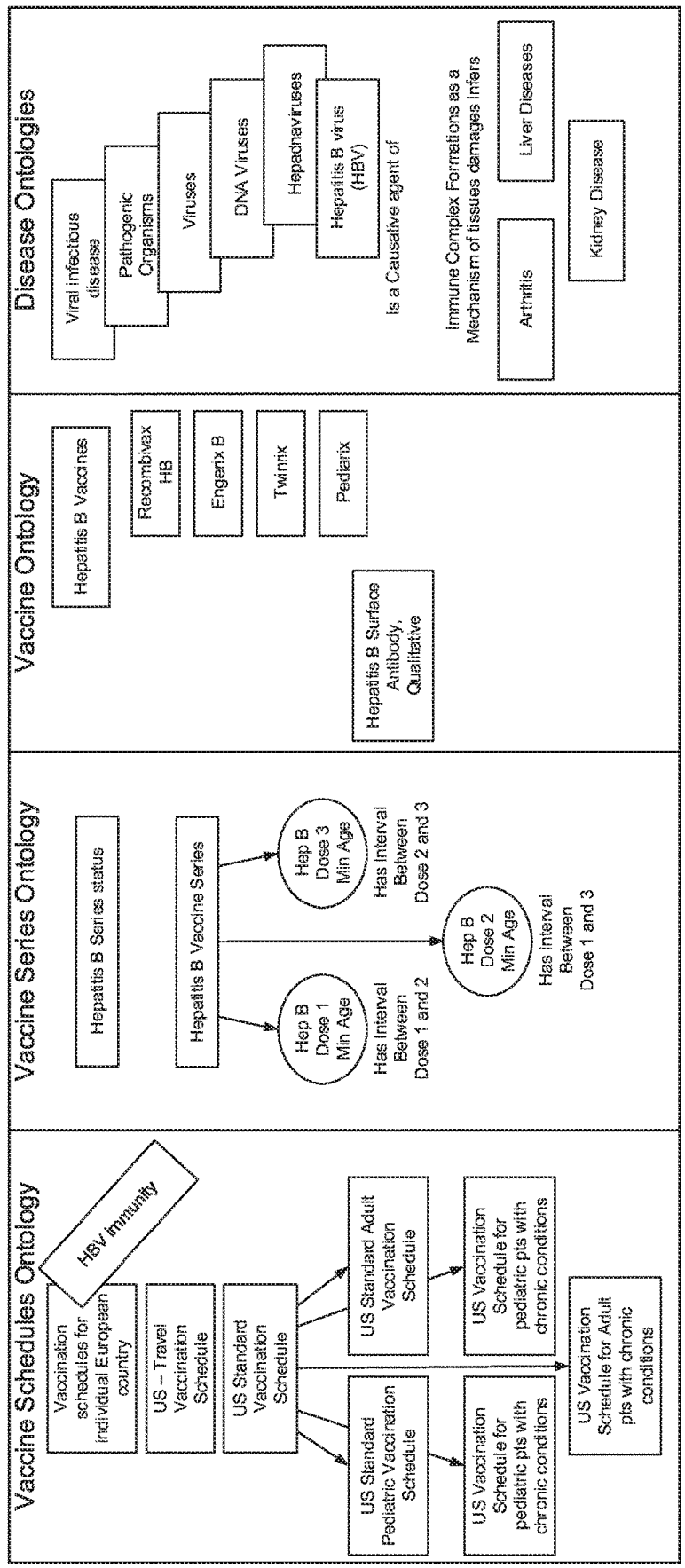
FIG. 1 depicts a simplified representation of an exemplary domain knowledge in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. Further, it will be apparent from this Detailed Description that the technological solutions disclosed herein are only a portion of those provided by the present invention. As such, the technological problems, solutions, advances, and improvements expressly referenced and explained should not be construed in a way that would limit the benefits and application of embodiments of the present invention.

In order for a computerized system to aggregate selected records and understand the information stored in electronic records, the computerized system applied rules to evaluate the selected records. A separate rule is used to evaluate each possible combination of variables and values for each variable that may be present in the record. Thus, a separate rule is drafted to address each and every distinct combination of variable(s) and/or values(s) for each variable. For example, in order to evaluate records for one condition (i.e., variable) having multiple available states (i.e., value), a rule is drafted for each distinct permutation of combinations that may be present in the record. As the amount of information stored in electronic records increases, the number and complexity of rules utilized escalates.

To illustrate, in order to for a computerized system to evaluate records involving five conditions, condition A having four available states, condition B having six available states, condition C having three available states, condition D having three available states, and condition E having four available states, the computerized system leverages a rule database storing a separate rule to evaluate each one of the 864 available permutations of the five conditions and available states. As such, rules database consumes vast amounts of physical memory in order to store the supportive rules for record evaluations involving hundreds or thousands of conditions. Additionally, a significant amount of processing resources are utilized to by the computerized system in order to execute the rules against records for evaluation involving hundreds or thousands of conditions. Further, each time that a change is made to one of the conditions and/or the available states for the conditions (e.g., new condition to add, a condition to remove, new state to add to a condition, and/or state to remove for a condition), the computer programming code for the corresponding rules is to be modified in an effort to keep the rules database up-to-date. As an additional difficulty, the complexity of the information stored in electronic records is growing faster than the capability available for scaling up the rules in a rules database.

The present invention represents a paradigm shift away from rules dependency. The present invention provides a contextually intelligent framework that leverages a contextualization mechanism in order to reduce a computerized system's dependence on rules and a rules database. By leveraging a contextualization mechanism, the present invention consumes less technological resources and more efficiently consumes technological resources (i.e., physical memory and processing power) relative to consumption in the absence of the in the absence of the systems, methods, and computer-readable media discussed hereinabove. Additionally, the present invention reduces the maintenance of keeping a rules database up-to-date and increase the capabilities for scaling-up a rules database with fewer rules (i.e., rule complexity increases while a total number of rules decreases), relative to computerized systems in the absence of in the absence of the systems, methods, and computer-readable media discussed herein. The embodiments herein also provide robust support for high level cognitive structures, maintains greater consistency and implicit relationships when modeling knowledge, and reduces the number of errors. Generally, the embodiments herein provide improved knowledge consistency and implicit relationships, relative to over other computerized systems operating in the absence of the systems, methods, and computer-readable media discussed herein.

Embodiments of the contextually intelligent framework perform refactoring of rules within a knowledge model. At a high level, refactoring reduces the number of rules and increases the number of concepts within a domain of an ontology, relative to other computerized systems operating in the absence of the contextualization mechanism. Accordingly, new concepts are identified and automatically used to generate new axioms based on the results of the refactoring methods discussed herein. By refactoring a knowledge model, the contextually intelligent framework modifies and improves the internal data structure of the knowledge model, while maintaining the desired external behavior of the knowledge model. For example, a single concept may be used to evaluate records with regard to Condition A. The one concept may, for example, replace n number of different rules that were initially drafted to evaluate Condition A in records. To illustrate refactoring of rules using the contextualization mechanism of the contextually intelligent framework, one concept might be used to replace 30 existing rules for evaluating electronic records for the clinical condition of spontaneous bacterial peritonitis and multiple available states for the clinical condition of spontaneous bacterial peritonitis. Additionally, because the enhanced knowledge model produced via the contextually intelligent framework has fewer rules after refactoring, the level of maintenance used for the enhanced knowledge model is reduced.

Additionally, refactoring rules in order to identify new concepts and axioms increases the diversity and depth of the domain knowledge of the knowledge model, and increases the "reusability" of the knowledge model across domains. For example, while a rule is generally drafted and inherently limited in its application to evaluate a particular concept (e.g., Condition A) and a particular domain, concepts and axioms are generally not limited in application to a particular concept and a particular domain. As such, concepts and axioms increase the reusability of the knowledge model across domains, which is an improvement over the limitations of rules alone.

Beginning with domain knowledge, domain knowledge refers to knowledge about the environment in which a system is operating. Exemplary domain knowledge includes clinical domain knowledge. Further examples of clinical domain knowledge include sepsis domain knowledge, unique electronic numbering domain knowledge (e.g., Bates numbering), and medical terminology domain knowledge (e.g., Medcin®, Systematized Nomenclature of Medicine (SNOMED)). FIG. 1 illustrates a simplified representation of an exemplary clinical domain knowledge. Domain knowledge may be encoded (i.e., using a computer language and/or data) as one or more sets of rules, forming a knowledge model. A knowledge model comprises a repository that stores the sets of rules representing the domain knowledge as structured data and unstructured data. The rules of the knowledge model encode the domain knowledge as statements in the form of an "if-then" (antecedent-consequent) sentence that describes logical inferences obtained from the domain knowledge and the knowledge model itself. FIG. 2 illustrates an exemplary set of domain specific rules 200. The knowledge model is capable of storing, analyzing, reasoning, and reusing knowledge, such that a knowledge model is highly specialized and distinct from a hierarchal database or a relational database, for example. The terms "knowledge base" and "knowledge model" are used interchangeably herein.

Figure 3:
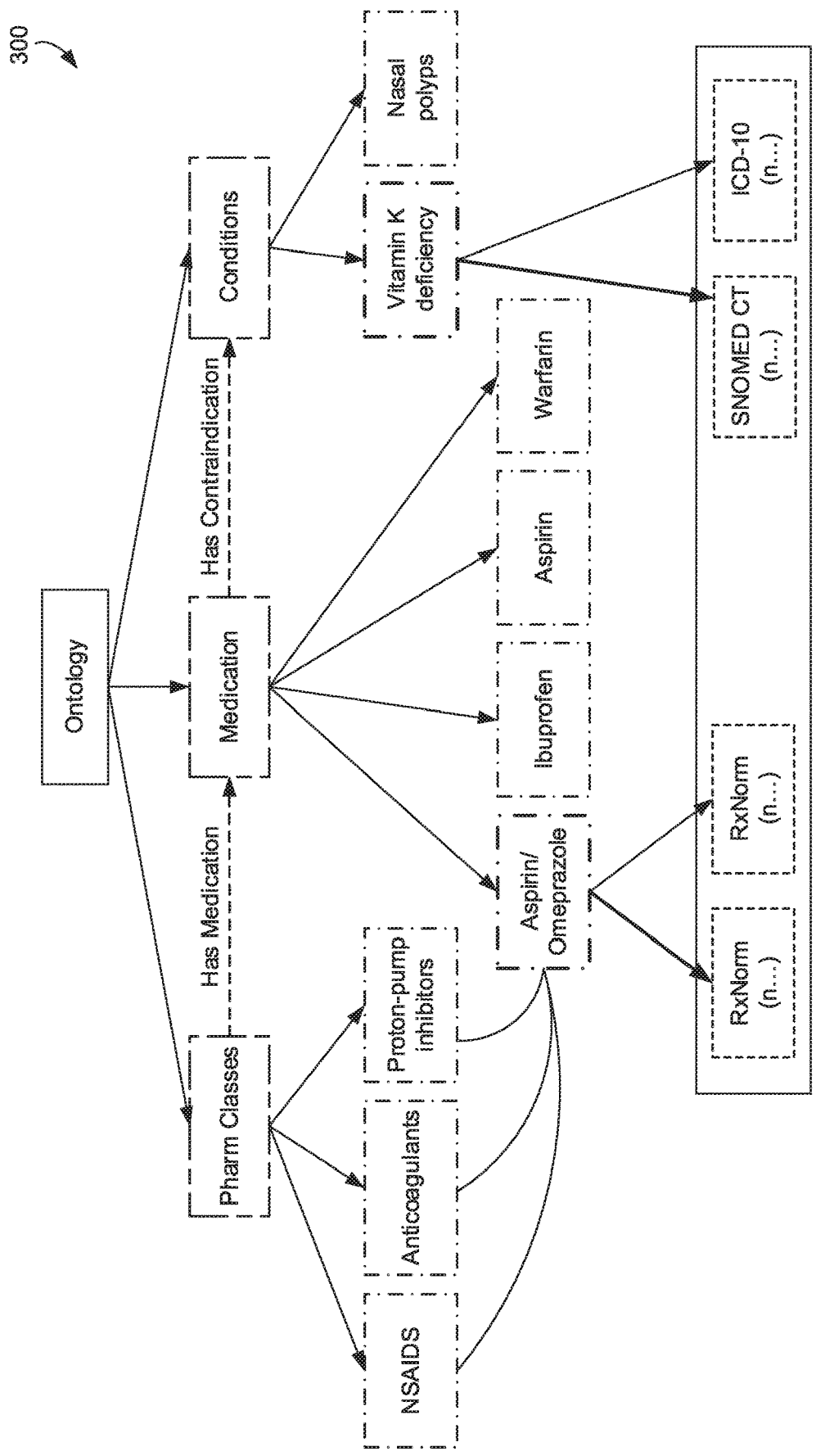
FIG. 3 depicts a simplified representation of exemplary ontology in accordance with an embodiment of the present invention.
Figure 4:
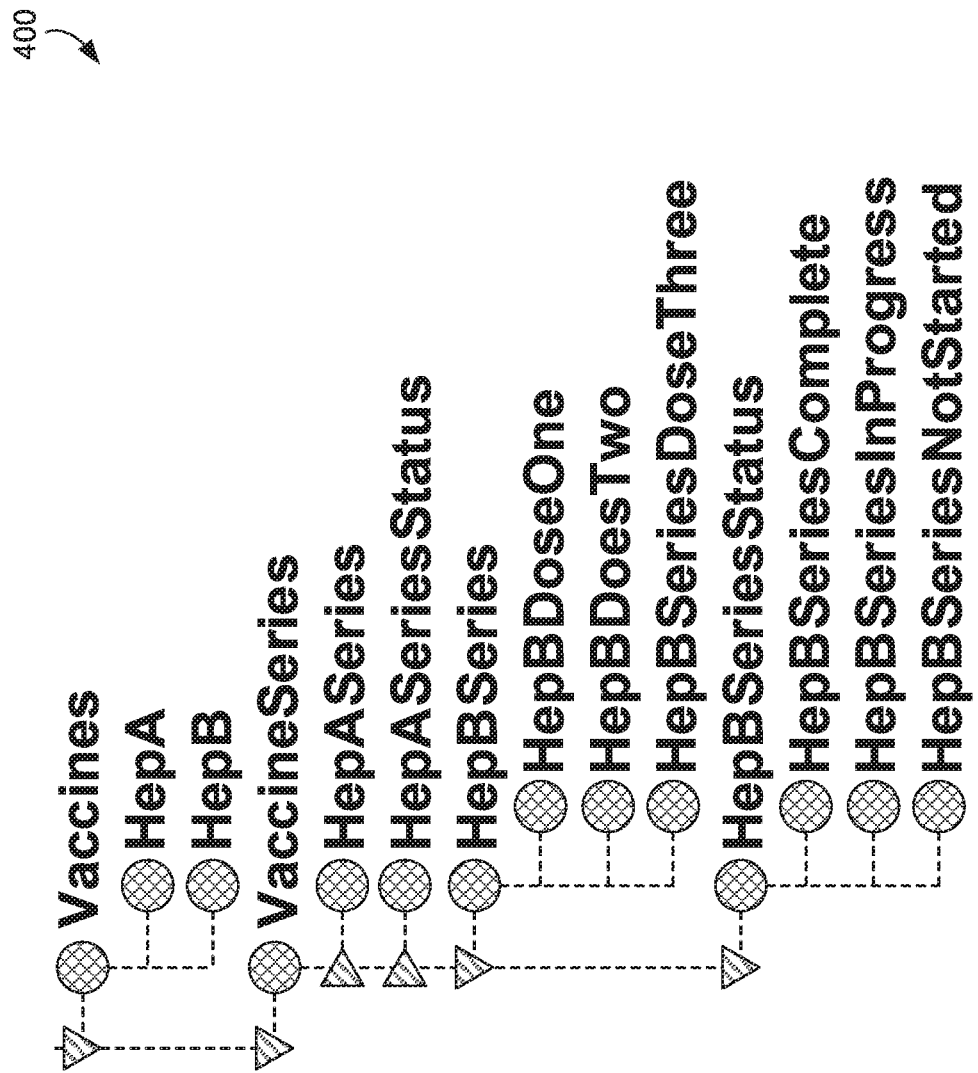
FIG. 4 depicts a simplified representation of an exemplary taxonomic hierarchy an ontology in accordance with an embodiment of the present invention.

While the knowledge model comprises a repository of rules for the domain knowledge, the knowledge model may also represent the domain knowledge using one or more ontologies. A domain ontology provides explicit, formal specifications of all of the terms within a domain knowledge and all of the relations among terms within the domain knowledge. FIG. 3 illustrates a simplified representation of exemplary ontology. Generally, a domain ontology uses classes and subclasses to explicitly describe concepts in the domain. A domain ontology comprises a representation, formal naming, and definition of categories, properties, and relations between concepts and data associated with the domain knowledge. Each object within a class and each object within a subclass may be referred to as an "instance." The classes, subclasses, and instances of the domain ontology may be represented in a taxonomic hierarchy. The terms "class" and "concept" are used interchangeably herein unless otherwise designated. FIG. 4 illustrates an exemplary taxonomic hierarchy of classes, subclasses, and/or instances of an ontology. The taxonomic hierarchy comprises a "tree" or a "backbone" representing the higher-level classes (i.e., corresponding to concepts in the domain knowledge) within the domain ontology, with subclasses and instances shown as nested nodes, wherein the nesting reflects the relations between classes, subclasses, and/or instances of an ontology. Generally, each class may have a designated "mode" that indicates a degree of certainty of the knowledge being represented. For example, a class representing Condition A may have a computer-determined mode of "Probable" or "Certain." Instances within that class may include "observations" having a computer-determined state (e.g., value has increased, decreased, value is normal, abnormal, within normal range, outside of normal range).

In addition to representing the relations between classes, subclasses, and instances through a taxonomic hierarchy, an ontology may be represented using axioms. An axiom refers to an assertion in a logical form that is distinguishable from the previously-described rules. Together, a plurality of axioms formulate an overall theory of the corresponding ontology, as the ontology describes of defines the corresponding domain. Axioms may include a theory derived from other axiomatic statements, for example, thus generating inferential knowledge within the domain knowledge. For example, the symbol "⊆" is used to state that one element is a subset of another element. To illustrate, the exemplary axiom x⊆y (read from left to right) is a statement that x is a subset of y. As such, the exemplary axiom x⊆y is a statement that x is contained in y, and/or that y contains x. Further, the exemplary axiom x⊆y is a statement that x is obtainable from y by removing zero or more elements, and/or that y is obtainable from x by adding zero or more elements. Generally, the symbol "⊂" is used in an axiomatic statement to define membership of an element to another element, the symbols "∩" or "∧" are used in an axiomatic statement to define a conjunction between two or more elements, and the symbols "∈" or "∨" are used in an axiomatic statement to define a disjunction between two or more elements. Accordingly, axioms are complex logical statements that are distinguishable from the relatively less complex "if-then" statements of the previously-described rules.

Having discussed domain knowledge, knowledge models, rules, ontologies, and axioms, the knowledge model discussed herein comprises a domain-ontology-based taxonomic hierarchy that represents rules, axioms, and the relations between classes, subclasses, and/or instances within the ontology. A computer system generally leverages such a knowledge model to solve complex problems. At a specific level, a knowledge-based computer system includes a knowledge model, a user interface, and an inference engine. However, it will be understood that the systems and methods described hereinafter are not limited to such computer systems, and may be operable locally or remotely, using web-based applications, the cloud, local and/or distributed networks, servers, virtual servers, and/or virtual machines, for example.

Rule Refactoring & Concept Identification

Figure 5:
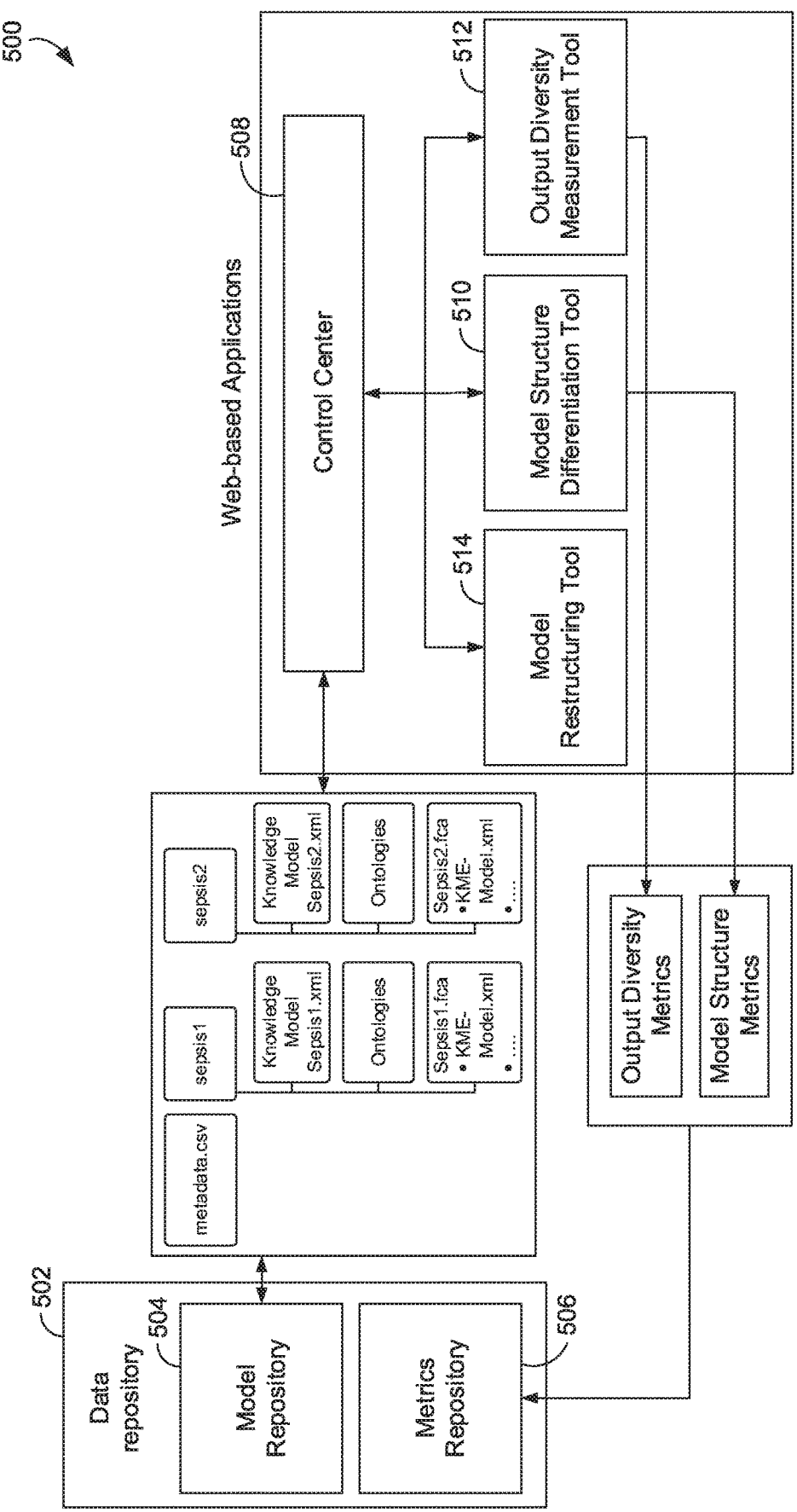
FIG. 5 depicts an exemplary system in accordance with an embodiment of the present invention.
Figure 6:
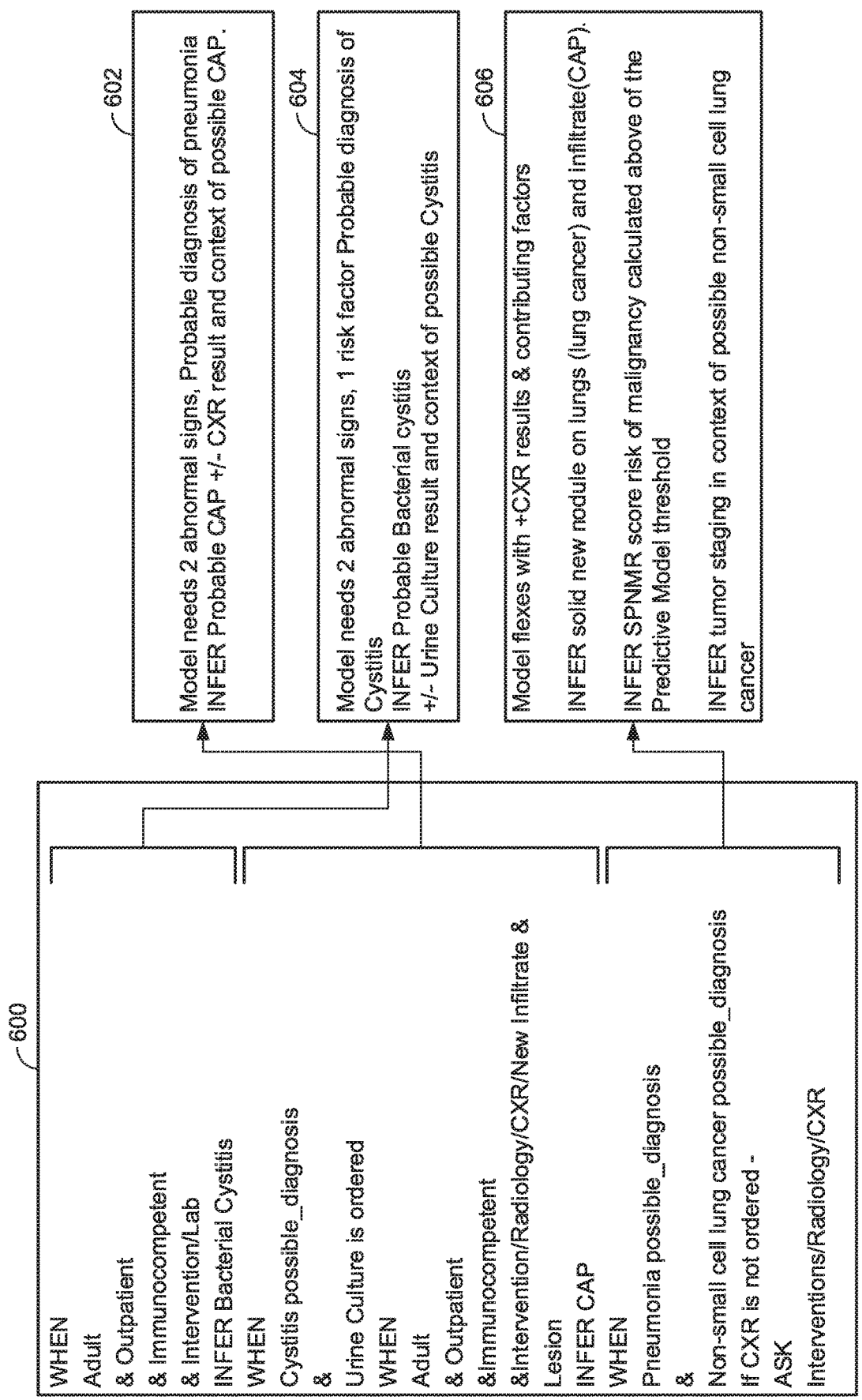
FIG. 6 depicts an exemplary model in accordance with an embodiment of the present invention.

Embodiments described herein operate to modify and improve an existing knowledge model by improving the internal structure (e.g., rules, axioms) of the knowledge model, while maintaining the external behavior of the knowledge model. The embodiments comprise systems, methods, and computer-readable media that refactor and restructure a knowledge model of a domain knowledge. In some embodiments the domain knowledge that is modeled by the knowledge model is a clinical domain knowledge involving one or more of problems, allergies, medicines, immunizations, conditions (e.g., sepsis, spontaneous bacterial peritonitis, or spontaneous bacterial peritonitis with sepsis). Beginning with FIG. 5, an exemplary system 500 is shown. The system 500 comprises a data repository 502 that stores data. The data repository 502 comprises a model repository 504 that stores a plurality of knowledge models. Each of the knowledge models may correspond to a different domain knowledge, in one example. In another example, each of the knowledge models may correspond to one domain knowledge. For example, the domain knowledge of the clinical condition of Sepsis may be represented by a first knowledge model for Sepsis, a second knowledge model for Sepsis, and a third knowledge for Sepsis, wherein each knowledge model is different and stored in the model repository 504. In this example, the model repository 504 stores a plurality of knowledge models, wherein at least a portion of the knowledge models correspond to the same or similar domain knowledge. In another example, the domain knowledge of Immunizations may be represented by a first knowledge model, the domain knowledge of Allergies may be represented by a second knowledge model, and another domain knowledge of Medicines (e.g., pharmaceuticals, treatments, and clinical interventions) is represented by a third knowledge model, wherein each knowledge model is different and stored in the model repository 504. A knowledge model comprises both explicit and implicit knowledge of the domain knowledge. For example, FIG. 6 presents an exemplary portion of a model 600 that represents explicit (e.g., "WHEN") and implicit (e.g., "INFER") domain knowledge. As such, the portion of the model 600 indicates how the model may generate implicit knowledge (e.g., inferences 602, 604, and 608) from explicit knowledge when values and conditions align. Such models of clinical domain knowledge are stored in the model repository 504 of the data repository 502. The data repository 502 further comprises a metrics repository 506 that stores a plurality of metrics reports. The metrics reports store information that quantify and describe the structure and complexity of the knowledge models, wherein the metrics reports are generated through one or more web-based applications, as discussed hereinafter.

The data repository 502, the model repository 504, and the metrics repository 506 may be managed and evaluated using one or more web-based applications. The web-based applications include a control center 508, through which a model structure differentiation tool 510, a model output diversity tool 512, and a model restructuring tool 514 are used to modify, and thus, improve the internal data structure (e.g., rules, axioms) of the knowledge model itself, while maintaining the external behavior of knowledge model. The control center 508 receives and reads one or more of the knowledge models stored in the model repository, in embodiments. For example, the control center 508 receives and reads a first model (e.g., sepsis 1) and a second model (e.g., sepsis 2) for handoff to the other web-based applications. For example, each knowledge model comprises a knowledge model having rules, axioms, and one or more ontologies. The control center 508 provides the one or more knowledge models to the model structure differentiation tool 510 and/or the model output diversity tool 512.

The model structure differentiation tool 510 receives one or more knowledge models from the control center 508. For example, the model structure differentiation tool 510 identifies a structure of a first knowledge model and identifies a structure of a second knowledge model. The term "structure" refers to one or more of the rules, axioms, taxonomic hierarchy of an ontology, rule maps, and a master document. In embodiments, the model structure differentiation tool 510 identifies the rules, axioms, taxonomic hierarchy, a rules maps, and a master document for each model received. When the model structure differentiation tool 510 receives two or more models, the model structure differentiation tool 510 may further determines differences between two or more of the models received. In further embodiments, the model structure differentiation tool 510 may determine differences an existing model prior to refactoring and said model after refactoring, as discussed hereinafter. For example, between a first and second model, the model structure differentiation tool 510 may recognize differences in one or more of: rules of the first model relative to rules of the second model, rule thresholds of the first model relative to rule thresholds of the second model, axioms of the first model relative to axioms of the second model, taxonomic hierarchy of the first model relative to taxonomic hierarchy of the second model, classes of the first model relative to classes of the second model, subclasses of the first model relative to subclasses of the second model rules mapping of the first model relative to a rules mapping of the second model, instances of the first model relative to instances of the second model and a master document of the first model relative to a master document of the second model. The model structure differentiation tool 510 may recognize each individual difference between two or more models relative to one another, for example. The model structure differentiation tool 510 may perform the identification of model structure and the recognition of structural differences between models corresponding to the same domain knowledge, in some embodiments. In other embodiments, the model structure differentiation tool 510 may perform the identification of model structure and the recognition of structural differences between models corresponding to the different and varied domain knowledge. For example, the model structure differentiation tool 510 may perform the identification of model structure and the recognition of structural differences between models corresponding to the same domain knowledge of Sepsis. In another example, the model structure differentiation tool 510 identify the structure of a Sepsis model structure and recognize structural differences between said model and a Spontaneous Bacterial Peritonitis model. Accordingly, the model structure differentiation tool 510 identifies and recognizes, based on the structure of one or more models, overlap in rules, axioms, taxonomic hierarchy, rules mapping, and master documents, independent of whether the models correspond to the same, similar, or different domain knowledge.

The model structure differentiation tool 510 generates a model structure metrics report comprising the structural metrics of each model alone, and/or the structural metrics of the model relative to one or more other models (e.g., a refactored version of a model). As discussed in detail hereinafter, the recognition of overlap between models (e.g., pre-refactoring and post-refactoring) provides the system 500 with insight and knowledge of how refactoring changes a model. Further, the recognition of overlap between models corresponding to different domain knowledge provides the system 500 with insight and knowledge of how refactoring changes to one model may inadvertently result in a change to another, second model. Inadvertent results may produce errors or negatively impact the performance of one or more models that are not being refactored at the time. Once generated, the model structure metrics report is communicated to the metrics repository 506, in some embodiments.

FIG. 7 provides an exemplary portion 700 of a model structure metrics report. The exemplary portion 700 of the model structure metrics report identifies specific individual differences between a first model (e.g., sepsis1 is a first model prior to refactoring) and a second model (e.g., sepsis1-fca is the first model as refactored), such as, for example, a total number of rules in the first model, a total number of rules in the second model, a number of rules that are present in the first model and absent from the second model, and a number of rules that are absent in the first model and present in the second model. The exemplary portion 700 of the model structure metrics report identifies specific individual differences between a first model (e.g., pre-refactoring sepsis1) and a second model (e.g., refactored sepsis1-fca), such as, for example, a total number of axioms in the first model, a total number of axioms in the second model, a number of axioms that are present in the first model and absent from the second model, and/or a number of axioms that are absent in the first model and present in the second model. Additionally or alternatively, the exemplary portion 700 of the model structure metrics report identifies specific individual differences between models, such as, for example, a total number of domain concepts in the first model, a total number of domain concepts in the second model, a number of domain concepts that are present in the first model and absent from the second model, and a number of domain concepts that are absent in the first model and present in the second model. As such, a model structure metrics report provides highly-granular, specific information as generated by the model structure differentiation tool 510.

In further embodiments, the model structure differentiation tool 510 generates metrics regarding the rules in each model. For example, the model structure metrics report may include one or more of a rule premise size, a rule consequence, a rule size, a nodes count (e.g., with regard to taxonomic hierarchy), a count of specific value premise nodes, referenced entities, and the like, as determined and recognized by model structure differentiation tool 510. FIG. 8 provides an exemplary portion 800 of a model structure metrics report that provides rule size distribution(s) of a first model and a second model. The model structure metrics report may also be communicated with or shared with the model output diversity tool 512 and/or the model restructuring tool 514, in some embodiments.

The model output diversity tool 512, receives one or more models from the control center 508, in embodiments. Additionally or alternatively, model output diversity tool 512, receives the model structure metrics report as input from the model structure differentiation tool 510. In embodiments, the model output diversity tool 512 determines the "fecundity" or diversity of a knowledge model. As such, the model output diversity tool 512 may determine complexity and depth of knowledge modeled by a first model (e.g., a model prior to refactoring) and a second model (e.g., said model subsequent to refactoring, or said model with anticipated changes to result when refactoring is implemented). Accordingly, the modifications and improvements to the internal structure of a knowledge model are quantifiable and visible via reports. In measuring the complexity and depth of the knowledge model, the model output diversity tool 512 determines a number of distinct forms capable of being created from the rules, axioms, and concepts in the model, traces and identifies the number of distinct paths within each individual form, identifies which concepts lead to the same form(s), and/or determines a distribution of path(s) that may be generated from each individual consideration. The terms "path," "output," and "end-state" are used interchangeably herein.

In one embodiment, the model output diversity tool 512 determines an overall output, output distribution, and/or output variation of a knowledge model, for example, pre-refactoring and/or post-refactoring. Generally, the overall output refers to a total number of distinct outputs a knowledge base is capable of generating. Accordingly, the overall outputs measures each and every distinct path that may be traced through the knowledge base, using the rules, axioms, and ontology of the knowledge base. Generally, the overall outputs does not consider overlap between paths such that two paths are determined to be distinct paths even through the two path may vary by only one different node, for example.

The output distribution refers to the distribution of the outputs capable of being produced, relative to other outputs produced by varied possible inputs. In simpler terms, the output distribution describes the distribution of outputs that may be produced by various inputs. Thus, the output distribution measures what variance of output may be produced by using all or many different inputs. The distribution of output values when charted may be clustered tightly together, or widely spread apart, for example. For example, when ten distinct inputs produce the same output, the ten distinct inputs are not widely distributed and are equivalent. In yet another example, when ten distinct inputs produce ten distinct outputs and the ten distinct outputs overlap each other at 90% in the output distribution, the ten distinct inputs may be recognized as equivalent (e.g., output-equivalent inputs). In another example, when both (K and $input^1 \Rightarrow output^1$) and (K and $input^2 \Rightarrow output^1$), the model output diversity tool 512 determines that $input^1$ and $input^2$ belong to the same equivalence class, such that $input^1$ and $input^2$ are output-equivalent inputs. In contrast, when (K and $input^1 \Rightarrow output^1$) and (K and $input^2 \Rightarrow output^2$), the model output diversity tool 512 determines that $input^1$ and $input^2$ do not belong same equivalence class, such that $input^1$ and $input^2$ are not output-equivalent inputs.

Output variation considers the degree of overlap between distinct paths (e.g., considers whether ten distinct paths only vary from one another by a single different node). The model output diversity tool 512 determines output variation. Output variation describes a measure of variance of the outputs (e.g., outputs are very different from one another, outputs are very similar to one another). Generally, output variation describes how distinct outputs are from one another. For example, when a distribution of all 50 outputs overlap each other at 90%, the output variation is 10% (e.g., relatively low) because the outputs are not different from one another. In contrast, for example, when 90% of the 50 distinct outputs do not overlap one another in the output distribution, the output variation diversity is relatively high. In further embodiments, the output variation may be considered when determining the output distribution. In one example, when (K and input$^1$=>output$^1$) and (K and input$^2$=>output$^2$), and output$^1$ and output$^2$ overlap one another in the output distribution, the model output diversity tool 512 may determine that input$^1$ and input$^2$ belong to the same equivalence class, such that input$^1$ and input$^2$ are output-equivalent inputs. The model output diversity tool 512 may generating an output diversity report including one or more of the overall output, output distribution, and output variation. The output diversity report is communicated to the metrics repository 506, in some embodiments. The output diversity report may also be communicated with or shared with the model structure differentiation tool 510 and/or the model restructuring tool 514.

The model restructuring tool 514 receives one or more models as input from the control center 508. For example, the model restructuring tool 514 received a first knowledge model to be evaluated and refactored. The model restructuring tool 514 refactors rules in the first knowledge model, in embodiments, in order to generate said knowledge model as restructured and improved. At a high level, refactoring is performed in order to cure an inefficiently structured knowledge model. An existing knowledge model may be inefficiently structured when rules are initially created using artificial and/or arbitrary thresholds (e.g., cutoff points) and the existing knowledge model may comprise many different rules, as initially generated for each and every iteration of a concept, as previously discussed. The model restructuring tool 514 refactors rules and generates axioms when restructuring the knowledge model, thus improving the structure of knowledge model and increasing the complexity and depth of the domain knowledge. Using the methods and computer-readable media discussed hereinafter, the system 500, which includes the model restructuring tool 514, restructures the knowledge base. The model restructuring tool 514 also generates results and exports the results to the model repository, in embodiments. In some embodiments, a refactored model is provided to the model structure differentiation tool 510 for generation of a model structure metrics report of the refactored model and/or is provided to the model output diversity tool 512 for generation of an output diversity report of the refactored model, as previously discussed.

Figure 9:
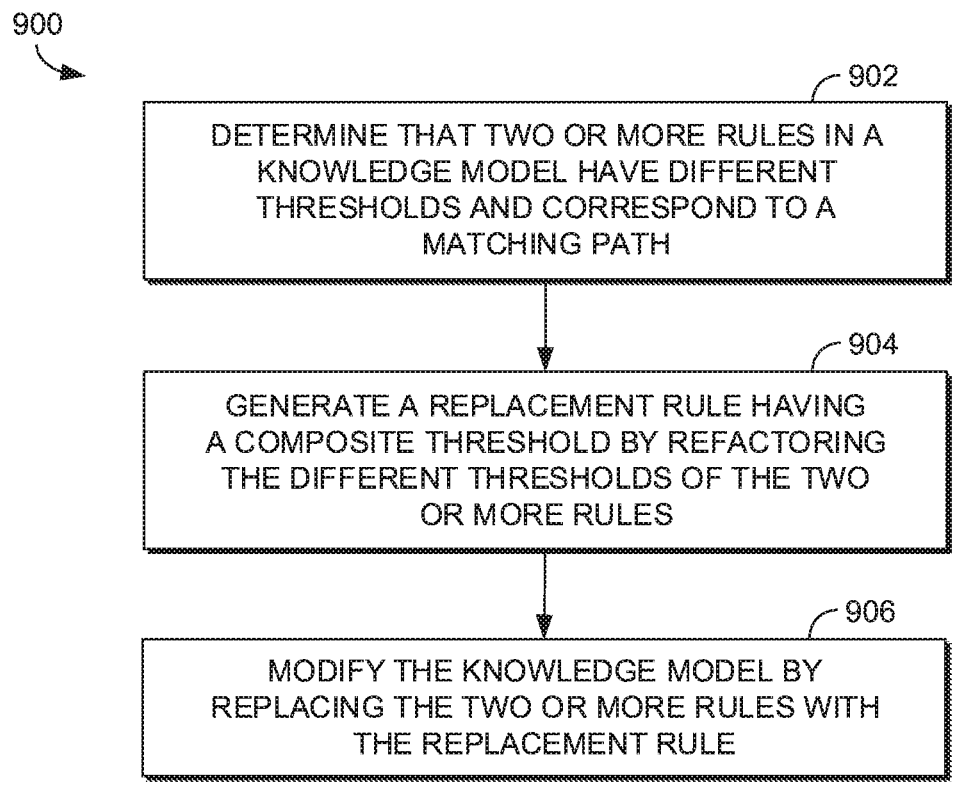
FIG. 9 depicts a flowchart of an exemplary method in accordance with an embodiment of the present invention.

Turning to FIG. 9, a flow chart representing an exemplary method 900 is presented in accordance with embodiments of the present invention. In some embodiments, the method 900 is performed via the system 500. In further embodiments, the method 900 is performed via the model restructuring tool 514. The method 900 may be a computerized method in an embodiment. In another embodiment, the method 900 may be performed by executing one or more computer-readable media having non-transitory instructions stored thereon using one or more processors.

In embodiments, the method 900 comprises determining that two or more rules in a knowledge model have different thresholds and correspond to a matching path, shown at block 902. For example, recalling FIG. 2, an exemplary set of domain specific rules are shown that reflect clinical domain knowledge of sepsis. As shown, the exemplary domain specific rules include various thresholds for a patient's age. As discussed previously, the exemplary domain specific rules may have been initially created using artificial and/or arbitrary thresholds (e.g., cutoff points). For example, a rule has been generated for various age ranges, with rule iterations involving values for blood pressure measurements obtained by a blood pressure cuff or blood pressure invasive and body temperatures, as shown in exemplary FIG. 2. The method 900 determines whether two or more domain specific rules in a knowledge model that have different thresholds also correspond to a matching path and/or the same output.

Figure 10:
FIG. 10 depicts a simplified representation of exemplary rules in accordance with an embodiment of the present invention.

For example, recalling FIG. 10, there are many rules 200 that reflect seven different age range thresholds and two different conditions (i.e., systolic blood pressure cuff, systolic blood pressure invasive). Within the exemplary rules, there are six different rules, each having different age ranges as thresholds for blood pressure (i.e., box 1002 (Age from 1 month)(Age up to 2 years), (Age from 0 day)(Age up to 1 week), (Age from 1 week)(Age up to 1 month), box 1004 (Age from 1 month)(Age up to 2 Years), (Age from 0 day)(Age up to 1 week), (Age from 1 week)(Age up to 1 month)). These six exemplary rules produce the same path such that all six rules share a "matching" path or output (i.e., (Systolic blood pressure) . . . [[is judged as VALUE decreased]]. In other words, when the same input n is evaluated against each of the six rules, the thresholds do not change the output of the rules such that the output is independent of the thresholds. Moreover, the rules may be determined to have matching paths, output, or end-states even when the rules reference different considerations such as methods of obtaining the input value (e.g., systolic blood pressure cuff, systolic blood pressure invasive). Boxes 1002 and 1004 are shown in FIG. 10 to visually group various domain specific rules in the knowledge model having different thresholds and having a matching path. Boxes 1006 and 1008 are shown in FIG. 10 to visually group various domain specific rules in the knowledge model having different thresholds and having a matching path. Boxes 1010 and 1012 are shown in FIG. 10 to visually group various domain specific rules in the knowledge model having different thresholds and having a matching path.

In another example shown in FIG. 10, eight different domain specific rules in the knowledge model, each having a different age range as a threshold of body temperature (i.e., Age from 0 day, Age up to 1 week), produce the same path, and thus, correspond to a matching path (i.e., all eight rules have an output, path, or end-state of [[is judged VALUE decreased]]). In such an example, when the same input n is evaluated against each of the eight rules, the various thresholds do not change the output, end-state, or path such that the eight rules are output-equivalents. Box 1014 is shown in FIG. 10 to visually group various domain specific rules in the knowledge model having different thresholds but that having a matching path. By determining that two or more rules in a knowledge model have different thresholds and determining that the two or more rules also correspond to a matching path, the two or more rules are used to generate one or more replacement rules, relatively condensed in number.

At block 904, the method 900 comprises generating a replacement rule having a composite threshold by refactoring the different thresholds of the two or more rules. In an embodiment, a single replacement rule is generated by refactoring several rules having varying thresholds and determined to correspond to the same path. For example, ten rules may be refactored in order to generate one single replacement rule. In another embodiment, multiple replacement rules are generated by refactoring of several rules such that the number of replacement rules is fewer than the original number of rules being refactored. In one example, ten rules may be refactored in order to generate five replacement rules having one or more new, refactored thresholds.

Figure 11:
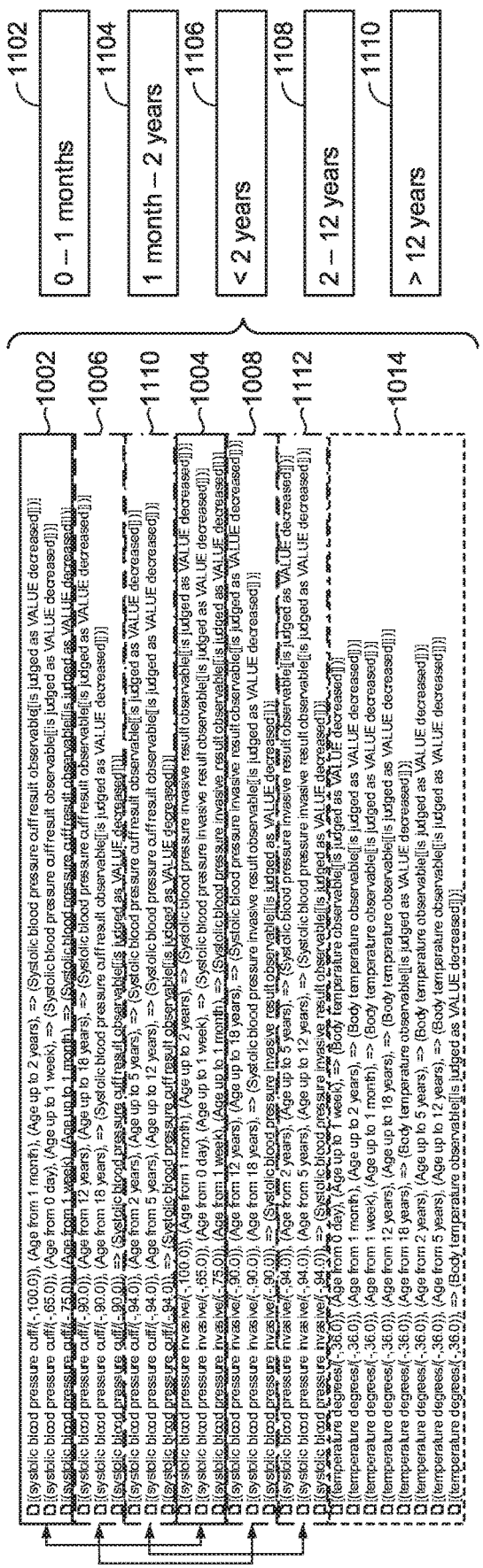
FIG. 11 depicts a simplified representation of exemplary rules in accordance with an embodiment of the present invention.

Turning to FIG. 11 as an example, the domain specific rules 200 of FIG. 2 determined to be output equivalents may be refactored to generate one or more replacement rules with new thresholds. All of the various age thresholds shown in the domain specific 200 (e.g., there are eight initial age ranges) may be condensed into five age ranges 1102, 1104, 1106, 1108, and 1110, as shown in FIG. 11, each new composite age range threshold reflecting the refactoring of the rules 200. For example, though now shown, the eight different domain specific rules for evaluating body temperature that have different age ranges as thresholds and all eight producing the same path (i.e., the output or end-state of [[is judged VALUE decreased]]), may be refactored to generate one replacement rule having a composite threshold of (Age from 0 day)(Age from 18 years). In some embodiments, generating the replacement rule having the composite threshold by refactoring the different thresholds of the two or more rules comprises merging the different thresholds of the two or more rules, wherein merging the different thresholds generates a composite threshold that comprises the different thresholds. As such, in some embodiments, a least a portion of the two or more rules are merged into one composite rule.

The method 900 further comprises modifying the knowledge model by replacing the two or more rules with the replacement rule, as presented at block 906. In an embodiment, a single replacement rule is generated from the refactoring of several rules having varying thresholds. Following the example of the eight different domain specific rules for evaluating body temperature, the one replacement rule having composite age threshold of (Age from 0 day) (Age from 18 years) may replace all eight of the existing rules within the knowledge model. Additionally or alternatively, because the eight rules indicated that the output decision of decrease in body temperature was produced (i.e., a same or matching path) regardless of an age, one new concept may be generated and used to replace the eight rules via the method 900. The new concept may be used to generate a new axiom that replaces the eight rules, in such embodiments. In modifying the knowledge model, the two or more rules may be removed or deleted from the knowledge model.

Continuing, the method 900 may be performed with respect to all rules within a knowledge model such that the entire knowledge model may be evaluated and refactored. By performing a refactoring directed to the whole knowledge model, for example, the number of rules in the knowledge base may be reduced, the average rule size may be reduced, the average size of an "if" premise (antecedent) in rules may be reduced, and/or the average size of a "then" statement (consequent) in rules may be reduced. Additionally or alternatively, by performing a refactoring with regard to all the rules in a knowledge model, for example, one or more additional concepts as axioms may be generated and added to the domain ontology of the knowledge model, wherein those additional concepts (i.e., represented as one or more new axioms) may be reused in one or more other domain ontologies (e.g., reusable axioms). The rules refactoring and generation of new concepts is such that the method 900 changed the structure of the domain knowledge and improves the domain knowledge itself. As such, the method 900 provides an improvement to domain knowledge and knowledge model technology.

In modifying one existing knowledge model by refactoring, the method 900 may further determine and recognize rule, axiom, and/or concept overlap between the knowledge model and other knowledge models in different domains, for example. As such, the method 900 has knowledge of exactly how refactoring a knowledge model may result in a change to another, second knowledge model, wherein those changes may produce errors or negatively impact the performance the second model. In some embodiment, the method 900 herein may utilize the model structure metrics report in order to provide recommendations for refactoring, prior to implementing the modifications. Exemplary recommendations and/or modifications to the knowledge model may include a recommendation to add a disjunctive axiom, one or more rules to remove as redundant to one another or redundant to an axiom, and/or rule refactoring and rules to merge. The recommendations may be provided to a user for review and approval prior to modifying the knowledge model, and/or may be exported to the model repository 504.

In further embodiments of the method 900, the method 900 comprises identifying a plurality of rules within the knowledge base. The method 900 may then determine a total number of different forms capable of being generated from the plurality of rules. Accordingly, the method 900 may determine a total number of different paths available within each one of the different forms. The method 900 may further comprise generating and/or receiving an output diversity report and a model structure metrics report for a knowledge model, before and/or after refactoring. As such, the method 900 may involve the model structure differentiation tool 510 and a model output diversity tool 512, as previously described, in addition to the model restructuring tool 514.

Additionally or alternatively, in some embodiments, the method 900 may comprise identifying, for each one of the different paths determined within each one of the different forms, at least one rule corresponding to the path. In some embodiments, the method 900 identifies, for each of the different forms, two or more rules that correspond to a matching path within the form. As such, each patch with a form may be evaluated in view of one or more rules. Then, the method 900 may recognize whether two or more rules that correspond to the matching path have different thresholds, for example. The identification of rule thresholds may be performed before or after identifying one or more shared paths within a form, in various embodiments.

Figure 12:
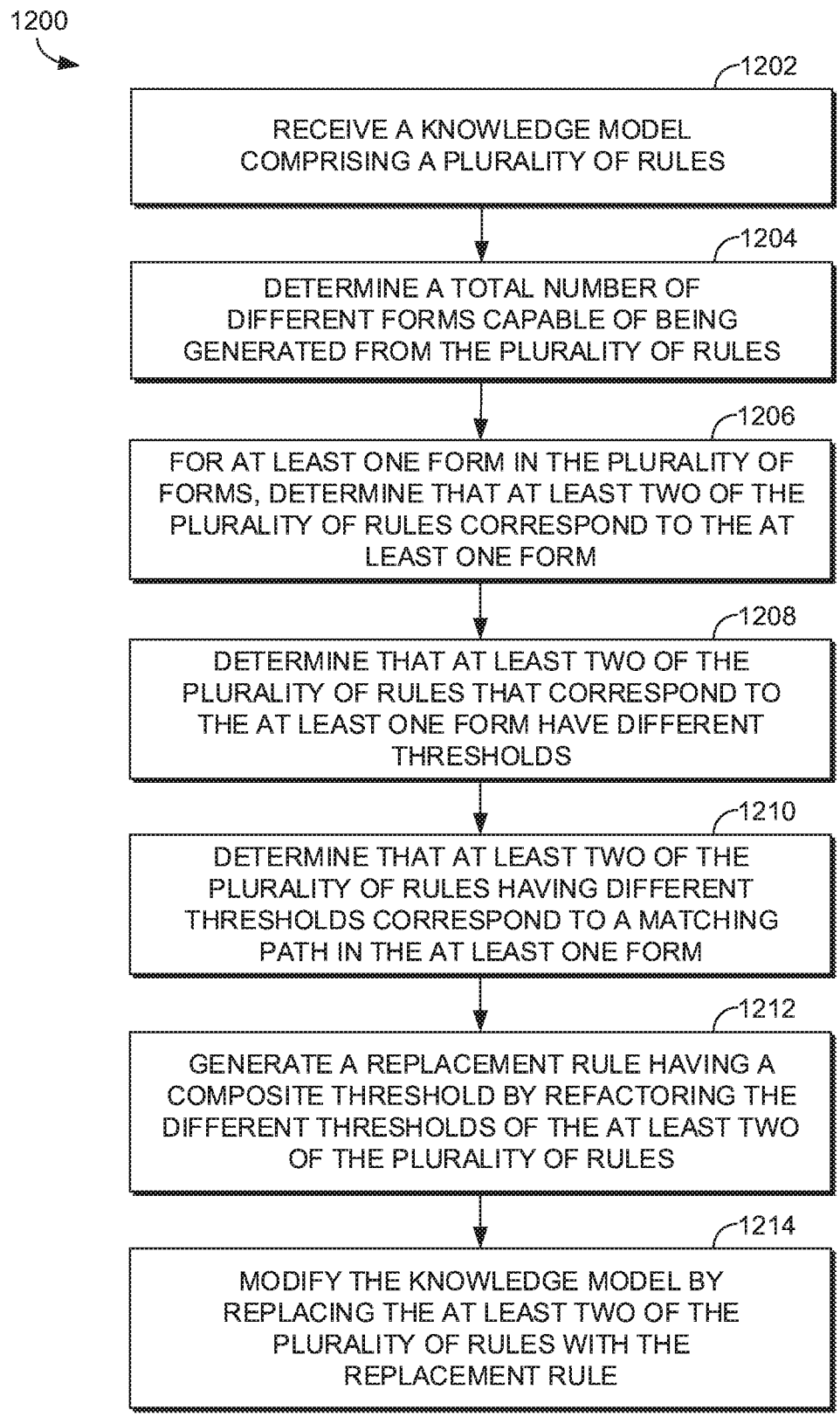
FIG. 12 depicts a flowchart of an exemplary method in accordance with an embodiment of the present invention.

Continuing to FIG. 12, a flow chart representing an exemplary method 1200 is presented in accordance with embodiments of the present invention. In some embodiments, the method 1200 is performed using the previously-described system 500. In further embodiments, the method 900 is performed using the model structure differentiation tool 510, the model output diversity tool 512 and the model restructuring tool 514, as previously described. The method 1200 may be a computerized method, in one embodiment. In another embodiment, the method 1200 may be performed by executing one or more computer-readable media having non-transitory instructions stored thereon using one or more processors.

At block 1202, the method 1200 receives a knowledge model comprising a plurality of rules. In further embodiments, the knowledge model further comprises a plurality of axioms and/or one or more ontologies. The knowledge model may be uploaded, for example, into one or more web-based applications that provide an interface for performing the method 1200 via one or more processors. At block 1204, the method 1200 determines a total number of different forms capable of being generated from the plurality of rules. The different forms may be identified and each available path may be traced within each form. In some embodiments, the method 1200 determines how many of the forms that are capable of being generated are also reusable for domain ontologies other that the domain ontology associated with the existing knowledge model. In yet another embodiment, the method 1200 determines a measure or degree of diversity between each of the distinct paths capable of generation within each form, for example. In some embodiments, the method 1200 may determine that two or more paths within one of the plurality of forms are input equivalent paths when the two or more path have a distribution overlap of at least 75%, 80%, or 90%. In one such embodiment, the method 1200 may determine that two or more paths within a form are matching paths based on a determination that the two or more paths are input equivalent paths. Thus, even though two or more paths within a form may not be identical, the relatively high degree of overlap between the two paths may be sufficient to determine, via one or more processors, that the two paths correspond to a matching path.

For at least one form in the plurality of forms, the method 1200 determines that at least two of the plurality of rules correspond to at least one form, as shown at block 1206. At block, 1208 the method 1200 determines that at least two of the plurality of rules that correspond to at least one form have different thresholds. At block 1210, the method 1200 determines that at least two of the plurality of rules having different thresholds correspond to a matching path in the at least one form. As previously discussed, rules may be determined to correspond to one path or to a matching path when the different thresholds in the rules do not effectuate a change to the path in the form, when the same value n is input to the two or more rules, for example.

At block 1212 the method 1200 generates a replacement rule having a composite threshold by refactoring the different thresholds of the at least two of the plurality of rules having different thresholds and corresponding to the matching path in the at least one form. (The generation of replacement rules has been discussed in detail previously and is not reiterated here for brevity). At block 1214, the method 1200 modifies the knowledge model by replacing the at least two of the plurality of rules with the replacement rule, as previously discussed. The method 1200 may be repeated for each rule within the plurality of rules of the knowledge model, in embodiments. As such, the entirety of the rules in the knowledge model may be refactored with respect to forms that may be generated.

Additionally or alternatively, the method 1200 may generate, via the one or more processors, at least one axiom based on refactoring the different thresholds of the at least one of the plurality of rules. In such an embodiment, the method 1200 modifies the knowledge model by adding the at least one axiom to the plurality of the axioms in the knowledge model. In another example, the method 1200 may generate, via one or more processors, at least one concept based on the refactoring. In such an example, the method 1200 modifies the knowledge model by adding the at least one concept to an ontology of the knowledge model. The addition of concepts to an ontology and axioms expressing the taxonomic hierarchy increases the complexity of the domain ontology and improves the reusability of the concepts in the knowledge model.

In one embodiment, the method 1200 further determines, via one or more processors, that one or more of the plurality of rules are redundant based on at least one of the plurality of axioms. To illustrate redundancy detection, an examination of the exemplary axiom $A \subset B$ (A is a subset of B), the rule A, $C \rightarrow D$ (a material conditional statement that if A, C are true, then D is also true), and the rule B, $C \rightarrow D$ (a material conditional statement that if B, C are true, then D is also true) reveals that the rule A, $C \rightarrow D$ is a redundant rule because the axiom defines that A is a subset of B and thus A is encompassed by the other rule B, $C \rightarrow D$. When a rules is determined to be redundant to other rules and/or to an axiom, the redundant rules may be filtered out of the rule pool prior to refactoring, via the method 1200. For example, the method 1200 may modify the knowledge model by removing or deleting the one or more of the plurality of rules that are determined to be redundant from the knowledge base.

Once a knowledge model is refactored using the systems and/or methods discussed above, the knowledge model having an improved internal structure may be implemented and leveraged by computer systems, as discussed hereinafter.

Records Reconciliation

At a high level, embodiments of the present invention utilize concept-based models, also known as ontology-based models, as discussed above with regard to knowledge models, to reconcile information currently stored in one system with information imported from a plurality of diverse systems, in order to generate recommendations that promote continuity of care in clinical settings. As such, a refactored knowledge model having an improved internal structure may be implemented and leveraged by computer systems, such that ontology-based models within the refactored knowledge model are applied to evaluate and reconcile electronic information.

At a practical level, other computerized systems are cumbersome and lack intelligence relative the systems, methods, and computer-readable media discussed herein. In an electronic medical information scenario, a clinician needs to navigate through a sequence of several GUIs before the clinician is able to comply with meaningful use requirements. The clinician imports information from multiple sources in different GUIs and compares the imported information presented on one GUI to the information currently on-file for a particular patient presented on another GUI (i.e., the clinician is navigating back and forth between different GUIs). The clinician then makes a decision as to whether the information currently on-file for a particular patient includes the imported information. All of these steps are repeated with regard to each of four different pieces of information in order to comply with meaningful use requirements: problems, allergies, medicines, and immunizations. Thus, the clinician has to slog through duplicate information, remember the information that they have visually seen, and then recognize when information is missing. This cumbersome compliance requirement is also repeated for every single patient encounter (e.g., a clinical visit or admission to a hospital).

Figure 13:
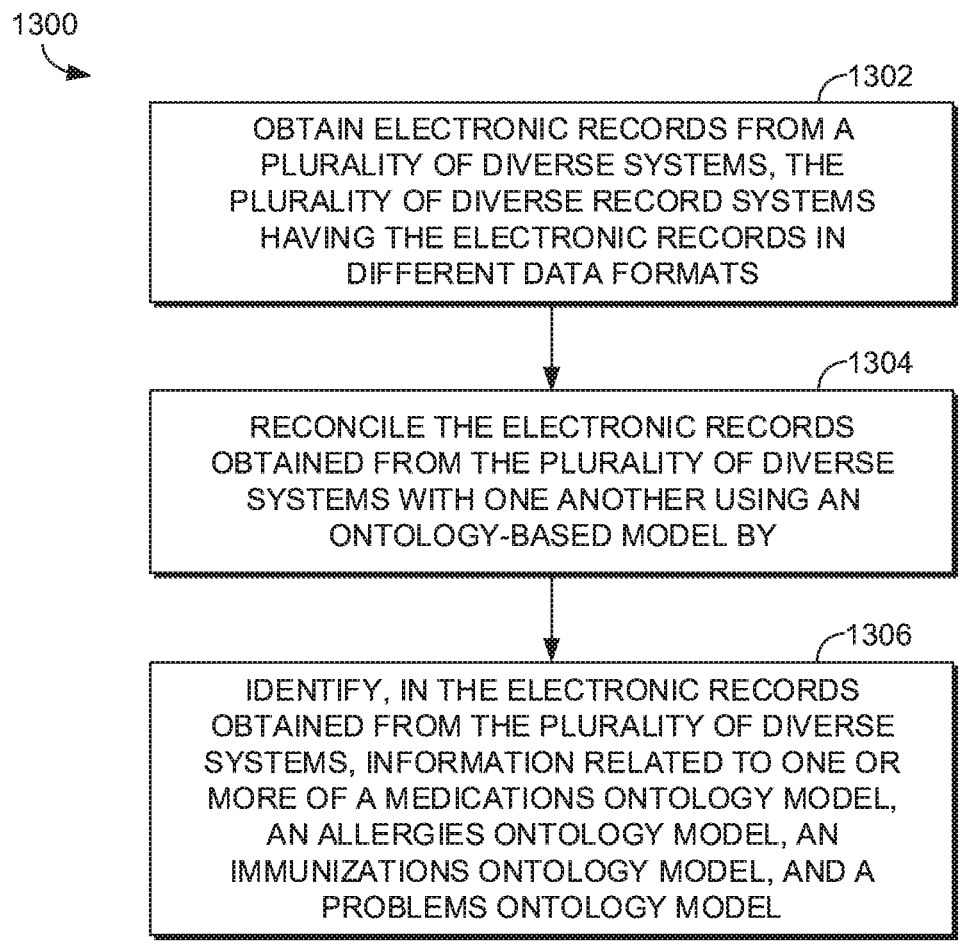
FIG. 13 depicts a flowchart of an exemplary method in accordance with an embodiment of the present invention.

FIG. 13 present an exemplary method 1300 in accordance with embodiments of the present invention. In some embodiments, the method 1300 is preformed subsequent to modifying the knowledge model by replacing the at least two of the plurality of rules with the replacement rule, as discussed above. The method 1300 may be a computerized method, in one embodiment. In another embodiment, the method 1300 may be performed by executing one or more computer-readable media having non-transitory instructions stored thereon using one or more processors.

In the method 1300, electronic records are obtained from a plurality of diverse systems, as shown at block 1302. The diverse systems having the records store and/or otherwise utilize the records in different data formats that may or may not be compatible with the other systems. In various embodiments, the electronic records obtained include registries (e.g., an immunization registry), electronic health records, electronic medical records, payer information, pharmacy records, laboratory information, employee information (i.e., which clinicians has, is, or will interact with a patient), and/or information captured by devices (i.e., data obtained from physiological monitoring devices capturing vital signs, etc.). The electronic records of each system may be stored in a particular format. Examples of data formats include HL7, FHIR, and XML.

The method 1300 reconciles the records obtained from the plurality of diverse systems with one another using an ontology-based model within the knowledge base, as illustrated at block 1304. In embodiments, reconciling the electronic records obtained from the plurality of diverse record systems comprises identifying, in the electronic records obtained from the plurality of diverse systems, information related to one or more of a medications ontology model, an allergies ontology model, an immunizations ontology model, and a problems ontology model.

In further embodiments, reconciling the electronic records obtained from the plurality of diverse record systems comprises applying one or more of the medications ontology model, the allergies ontology model, the immunizations ontology model, and the problems ontology model to the electronic records obtained from the plurality of diverse systems. Based on the application of one or more of the medications ontology model, the allergies ontology model, the immunizations ontology model, and the problems ontology model to the electronic records, recognizing discrete data items that are relevant to a meaningful use decision regarding one or more of medications, allergies, immunizations, and problems. In an embodiment, reconciling the electronic records obtained from the plurality of diverse record systems includes performing one or more of data cleansing, data standardization, concept or ontology normalization, records prioritization, and person matching on the electronic records.

Figure 14:
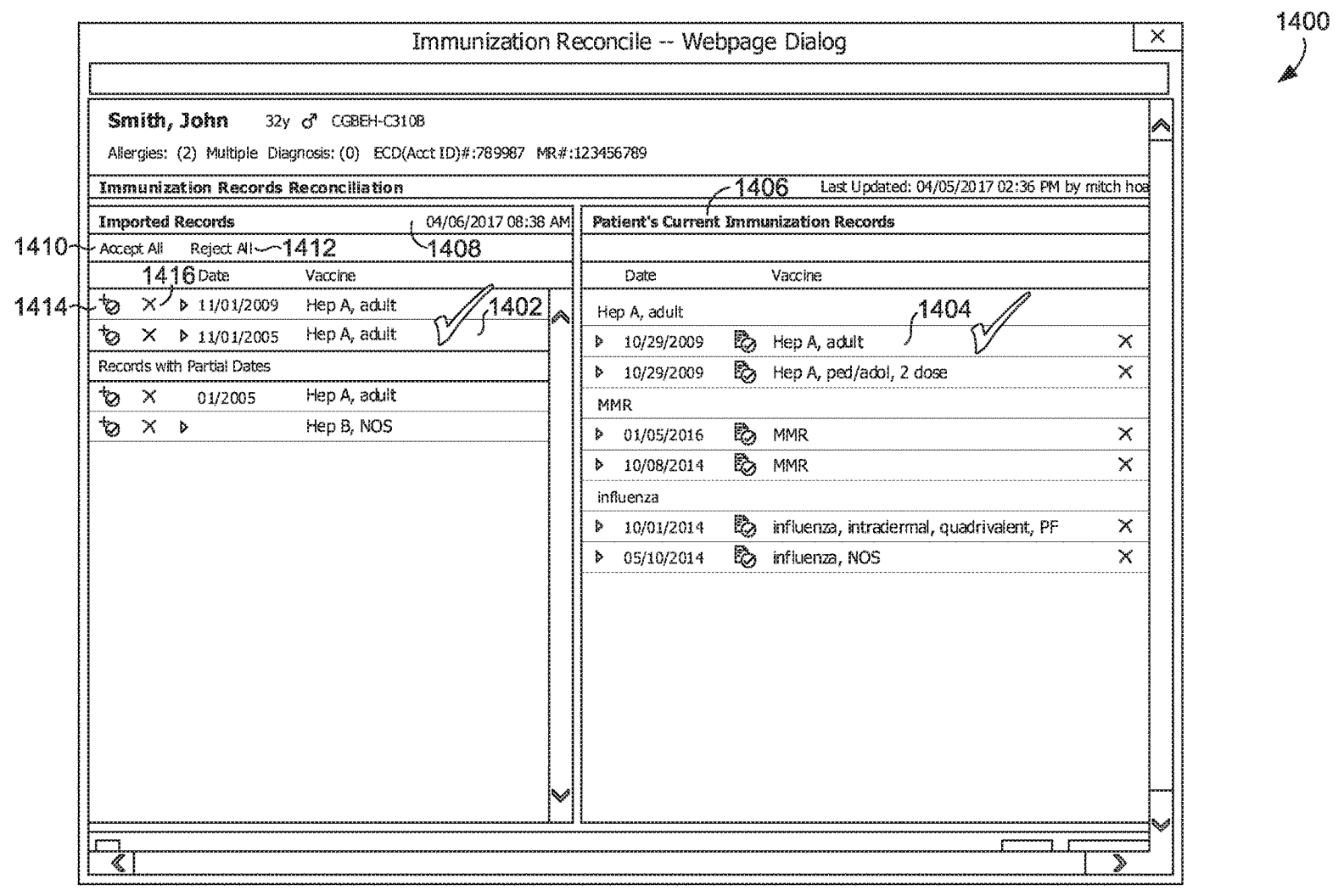
Figure 15:
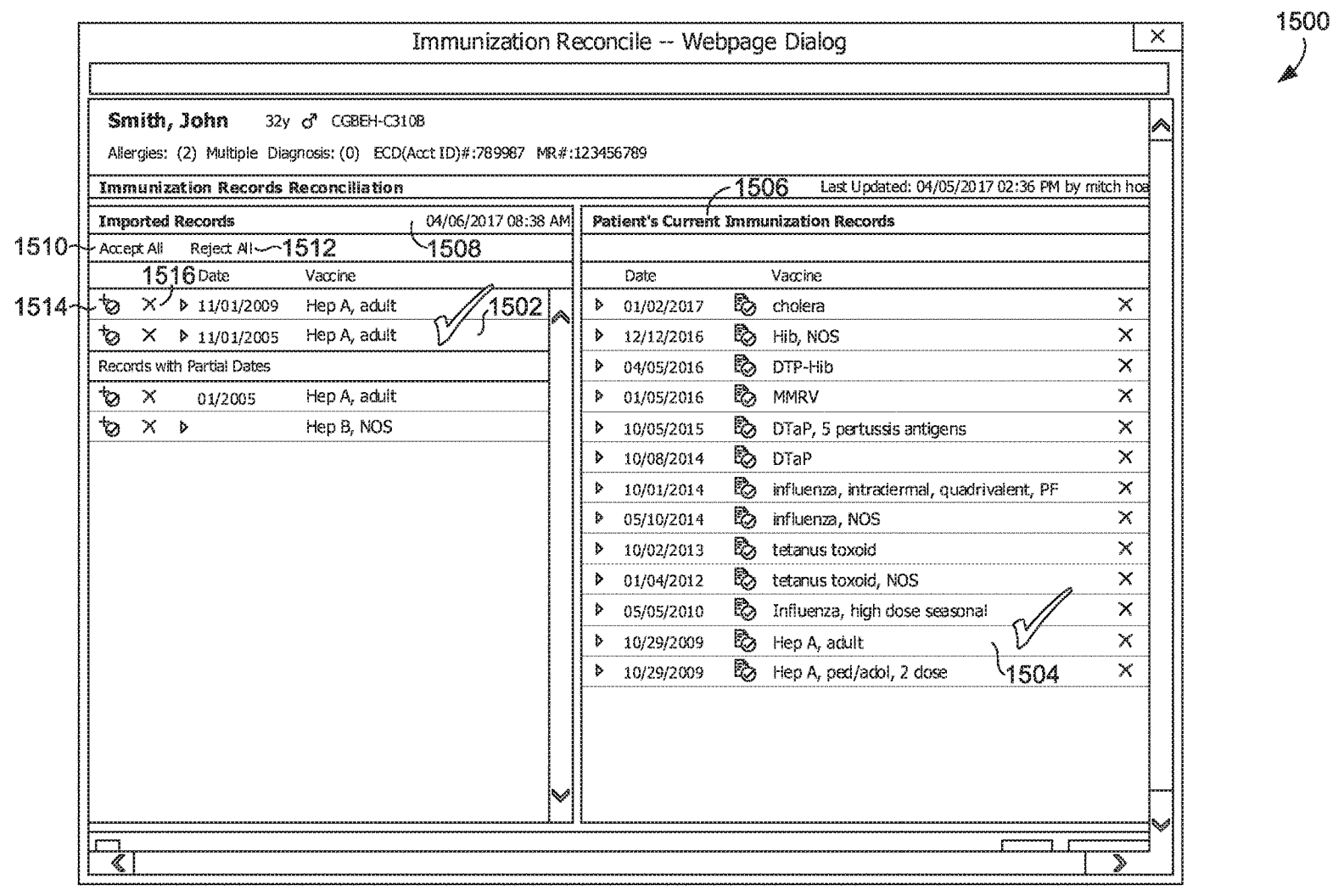

The method 1300 continues by generating inferential knowledge based on reconciling the record, as shown at block 1306. In an embodiment, generating inferential knowledge based on the discrete data items recognized as being relevant to a meaningful use decision regarding one or more of medications, allergies, immunizations, and problems. Additionally or alternatively, generating inferential knowledge comprises applying a forecasting model to the discrete data items, the forecasting model being specific to one of medications, allergies, immunizations, or problems. Based on applying the forecasting model to the discrete data items, a recommendation specific to one of medications, allergies, immunizations, or problems may be generated, in some embodiments. For example, FIG. 14 provides an exemplary GUI 1400. The GUI 1400 includes one or more recommendations 1402 and 1404 to reconcile a patient's existing vaccination record 1406 with an imported record 1408 for the patient. The single GUI 1400 presents the patient's existing vaccination record 1406 in one pane side-by side with the imported records 1408 for the patient in another pane such that a user viewing the GUI 1400 does not need to navigate back and forth between different GUIs, screens, tabs, or the like. The recommendation requests a user input to confirm or deny the recommendation. For example, the GUI 1400 includes user-selectable options to Accept All recommendations 1410, Reject All recommendations 1412, as well as individually selectable options 1414 and 1416 to accept or reject each recommendation regarding the imported records 1408. When a user input confirms the recommendation, records are merged in an electronic health record for a patient and reconciliation for that particular information and the particular patient is concluded with regard to meaningful use compliance, for example. In another example, FIG. 15 provides an exemplary GUI 1500. The GUI 1500 includes one or more recommendations 1502 and 1504 to reconcile a patient's existing vaccination record 1506 with imported records 1508 for the patient. The single GUI 1500 presents the patient's existing vaccination record 1506 side-by side with the imported records 1508 for the patient such that a user viewing the GUI 1500 does not need to navigate back and forth between different GUIs. The recommendation requests a user input to confirm or deny the recommendation. For example, the GUI 1500 includes user-selectable options to Accept All recommendations 1510, Reject All recommendations 1512, as well as individually selectable options 1514 and 1516 to accept or reject each recommendation regarding the imported records 1508.

Upon merging, patient care opportunities may be identified based on the inferential knowledge, in accordance with the method 1300. For example, having merged selected and user-confirmed records on immunizations from diverse systems, the method 1300 recognizes the patient is overdue to receive one vaccination and is approaching a deadline to receive another vaccination that is not yet overdue. The method 1300 may enable a clinical user to enter a medical order or may auto-populate a medical order for that patient to address the patient care opportunities. Accordingly, the method 1300 generates inferential knowledge including patient's immunization status, a reason for the patient to be vaccinated, and a suggested vaccination opportunity, which are all provided to a clinician user when records are merged in an electronic health record for a patient, for example.

In some embodiments, reconciling the electronic records obtained from the plurality of diverse systems with one another includes identifying information in the electronic records that is not present in at least one of the plurality of systems. In one embodiment, the method 1300 updates the at least one of the plurality of systems to include the identified information.

The methods discussed herein may be performed using a contextually intelligent framework. The contextually intelligent framework comprises a content management workspace, a content component definition model, a discern ontology, and electronic health records. The contextually intelligent framework integrates these components, which represent content, content definitions, and models, with one another for interoperability and for ontology-guided reconciliation of electronic records. Because these components and/or tools are integrated together to create the contextually intelligent framework, the contextually intelligent framework prevents data and information from being kept in separate silos.

The content management workspace is a knowledge management system that supports structured clinical knowledge and terminology mapping, referencing, authoring, and license version management. The content component definition model is a model of reason over knowledge. The content component definition model provides contextualization of complex medical situations, supports clinical ontology, document models, bridge rules, analytics, and implicit relationships. The content component definition model further comprises multiple models of all questions and term hierarchies, for example. The content component definition model includes correlators, interpreters, data items, and attributes of data items, in embodiments.

The discern ontologies provides a framework of concepts and concept templates. The discern ontology relies on specific pathways or "trees." The content management workspace and the discern ontologies may comprise information regarding content definitions (e.g., standards, orders, diagnostics, education, and template questions). Additionally or alternatively, the content component definition model builds on the discern ontology's concepts and concept templates.

The electronic health records are a source of current patient context, meaning that the electronic records include information as to what is known for a patient at the current point in time. In embodiments, the electronic health records are being reconciled with the information imported from a plurality of diverse systems, via the methods described herein and implemented through the contextually intelligent framework.

Continuing, the contextually intelligent framework may be implemented in various ways. In one example, a system comprises a retrieval service, the contextually intelligent framework, and electronic health records and/or clinical workflows. In an embodiment, the retrieval service obtains, accesses, or otherwise retrieves a plurality of electronic records from diverse systems. In the context of meaningful use requirements, the retrieval service may perform patient information gathering for one or more of problems, allergies, medicines, immunizations, and in some embodiments, sepsis. The retrieval service may analyze the configuration of each of the diverse systems and the electronic records retrieved from each of the diverse systems. The retrieval service may prioritize one of the diverse systems over the other systems, for example. The retrieval service may create an order of importance or priority for the diverse systems, in some embodiments. The retrieval service may further group electronic records together or apart to reflect the diverse system from which the retrieval service obtained the electronic records. In the system, the retrieval service may perform a de-duplication of the electronic records. The retrieval service may group and/or sort the electronic records, as well. For example, when grouping records, the retrieval service may group two records together such that only one of the electronic records is hidden and another record, in said group, is shown to the system.

In an alternative embodiment of the system, the contextually intelligent framework performs a de-duplication of the electronic records processed by the retrieval service. The contextually intelligent framework may group and/or sort the electronic records, in such an embodiment. For example, when grouping records, the contextually intelligent framework may group two records together such that only one of the electronic records is hidden and another record, in said group, is shown to the system.

Continuing, in the system, the contextually intelligent framework applies forecasting models to the electronic records, as processed by the retrieval service. One or more forecasting models may be applied to electronic records corresponding to the patient for which information is being reconciled. In some embodiments, a model that is specific to problems, allergies, medicines, immunizations, or in some embodiments, sepsis, is applied. The forecasting model is ontology-based, such that the information being reconciled for a particular patient is placed into the context of a problem-specific ontology, an allergies-specific ontology, a medicine-specific ontology, an immunizations-specific ontology, or a sepsis-specific ontology, for example. The forecasting model is used to recognize, based on the patient information mapped to a specific ontology, recommendations to place a medical order for the patient, for example, wherein the medical order promotes continuity of care for the patient.

The forecasting model provides the patient information, as mapped to a specific ontology, for reconciliation recommendations regarding another electronic health record and/or for providing the orderable recommendations to a clinician user via a clinical workflow. In embodiments, the forecasting model provides advanced decision support regarding one or more of meaningful use reconciliation requirements, problems, allergies, medications, and immunizations. As such, a reconciliation recommendation and/or an orderable recommendation may be output from the contextually intelligent framework. Reconciliation is achieved based on user input to confirm the reconciliation recommendation, at admission, discharge, and/or another time point regarding a patient encounter or clinical documentation. The orderable recommendations may be integrated automatically into one or more clinical workflows corresponding to the patient for which information is being reconciled.

Figure 16:
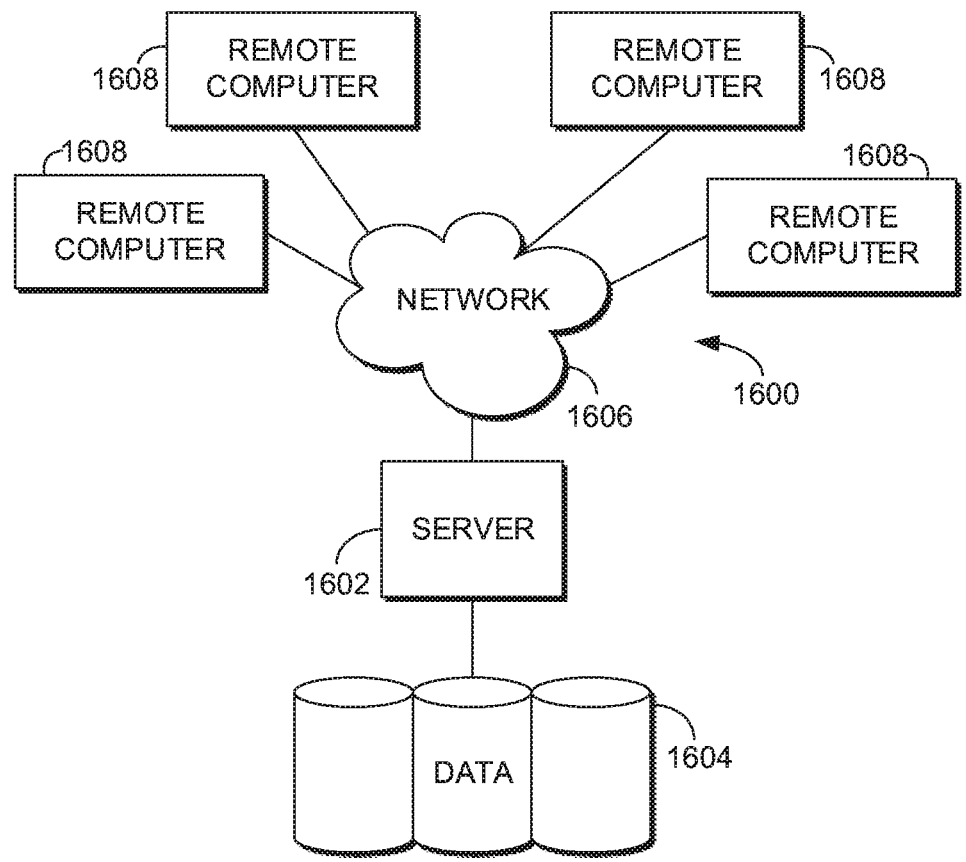
FIG. 16 depicts an exemplary computing environment in accordance with an embodiment of the present invention.

Hereinafter, an exemplary computing environment is described with regard to the systems, methods, and computer-media described hereinabove. Turning to FIG. 16, an exemplary computing environment is depicted, in accordance with an embodiment of the present invention. It will be understood by those of ordinary skill in the art that the exemplary computing environment 1600 is just one example of a suitable computing environment and is not intended to limit the scope of use or functionality of the present invention. Similarly, the computing environment 1600 should not be interpreted as imputing any dependency and/or any requirements with regard to each component and combination(s) of components illustrated in FIG. 16. It will be appreciated by those having ordinary skill in the art that the connections illustrated in FIG. 16 are also exemplary as other methods, hardware, software, and devices for establishing a communications link between the components, devices, systems, and entities, as shown in FIG. 16, may be utilized in implementation of the present invention. Although the connections are depicted using one or more solid lines, it will be understood by those having ordinary skill in the art that the exemplary connections of FIG. 16 may be hardwired or wireless, and may use intermediary components that have been omitted or not included in FIG. 16 for simplicity's sake. As such, the absence of components from FIG. 16 should be not be interpreted as limiting the present invention to exclude additional components and combination(s) of components. Moreover, though devices and components are represented in FIG. 16 as singular devices and components, it will be appreciated that some embodiments may include a plurality of the devices and components such that FIG. 16 should not be considered as limiting the number of a device or component.

Continuing, the computing environment 1600 of FIG. 16 is illustrated as being a distributed environment where components and devices may be remote from one another and may perform separate tasks. The components and devices may communicate with one another and may be linked to each other using a network 1602. The network 1602 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 1602, generally, provides the components and devices access to the Internet and web-based applications.

The computing environment 1600 comprises a computing device in the form of a server 1604. Although illustrated as one component in FIG. 16, the present invention may utilize a plurality of local servers and/or remote servers in the computing environment 1600. The server 1604 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 1604 may include or may have access to computer-readable media. Computer-readable media can be any available media that may be accessed by server 1604, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 1604. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the server 1604 uses logical connections to communicate with one or more remote computers 1606 within the computing environment 1600. In embodiments where the network 1602 includes a wireless network, the server 1604 may employ a modem to establish communications with the Internet, the server 1604 may connect to the Internet using Wi-Fi or wireless access points, or the server may use a wireless network adapter to access the Internet. The server 1604 engages in two-way communication with any or all of the components and devices illustrated in FIG. 16, using the network 1602. Accordingly, the server 1604 may send data to and receive data from the remote computers 1606 over the network 1602.

Although illustrated as a single device, the remote computers 1606 may include multiple computing devices. In an embodiment having a distributed network, the remote computers 1606 may be located at one or more different geographic locations. In an embodiment where the remote computers 1606 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 1606 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 1606 may be physically located in a non-medical setting, such as a packing and shipping facility or deployed within a fleet of delivery or courier vehicles.

Continuing, the computing environment 1600 includes a data store 1608. Although shown as a single component, the data store 1608 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 1608 includes physical memory that is configured to store information encoded in data. For example, the data store 1608 may provide storage for computer-readable instructions, computer-executable instructions, data structures, data arrays, computer programs, applications, and other data that supports the functions and action to be undertaken using the computing environment 1600 and components shown in exemplary FIG. 16.

In a computing environment having distributed components that are communicatively coupled via the network 1602, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the server 1604 may access, retrieve, communicate, receive, and update information stored in the data store 1608, including program modules. Accordingly, the server 1604 may execute, using a processor, computer instructions stored in the data store 1608 in order to perform embodiments described herein.

Although internal components of the devices in FIG. 16, such as the server 1604, are not illustrated, those of ordinary skill in the art will appreciate that internal components and their interconnection are present in the devices of FIG. 16. Accordingly, additional details concerning the internal construction device are not further disclosed herein.

Also, the present invention has been described in relation to particular embodiments, which are intended in all respects to be illustrative rather than restrictive. Thus the present invention is not limited to these embodiments, but variations and modifications may be made without departing from the scope of the present invention.

What is claimed is:

1. A computerized method comprising:
   obtaining electronic records from a plurality of diverse systems, the plurality of diverse record systems having the electronic records in different data formats;
   reconciling the electronic records obtained from the plurality of diverse systems with one another using an ontology-based model; and
   generating inferential knowledge based on reconciling the electronic records, wherein generating the inferential knowledge comprises:
      applying a forecasting model to the electronic records as reconciled, the forecasting model being specific to one of medications, allergies, immunizations, or problems; and
      based on applying the forecasting model, generating a reconciliation recommendation to reconcile two or more of the electronic records.

2. The method of claim 1, wherein reconciling the electronic records obtained from the plurality of diverse systems comprises:
   identifying, in the electronic records obtained from the plurality of diverse systems, information related to one or more of a medications ontology model, an allergies ontology model, an immunizations ontology model, and a problems ontology model.

3. The method of claim 1, wherein reconciling the electronic records obtained from the plurality of diverse systems comprises:
   applying one or more of a medications ontology model, an allergies ontology model, an immunizations ontology model, and a problems ontology model to the electronic records obtained from the plurality of diverse systems; and
   based on the application of one or more of the medications ontology model, the allergies ontology model, the immunizations ontology model, and the problems ontology model to the electronic records, recognizing discrete data items that are relevant to a meaningful use decision regarding one or more of medications, allergies, immunizations, and problems.

4. The method of claim 3, further comprising generating inferential knowledge based on the discrete data items recognized as being relevant to a meaningful use decision regarding one or more of medications, allergies, immunizations, and problems.

5. The method of claim 1, wherein the electronic records are stored in two or more of an HL7 data format, an FHIR data format, and an XML data format.

6. The method of claim 1, wherein reconciling the electronic records obtained from the plurality of diverse systems with one another comprises:
   identifying information in the electronic records that is not present in at least one of the plurality of diverse systems; and
   updating the at least one of the plurality of diverse systems to include the identified information.

7. The method of claim 1, wherein reconciling the electronic records obtained from the plurality of diverse systems comprises performing two or more of data cleansing, data standardization, concept normalization, records prioritization, and person matching.

8. A computerized method comprising:
   obtaining electronic records from a plurality of diverse systems having electronic records in different data formats;
   reconciling the electronic records obtained from the plurality of diverse systems with one another using an ontology-based model in a knowledge model by:
      applying one or more of a medications ontology model, an allergies ontology model, an immunizations ontology model, and a problems ontology model to the electronic records; and
      recognizing discrete data items that are relevant to a meaningful use decision regarding one or more of medications, allergies, immunizations, and problems; and
   generating inferences based on the discrete data items recognized as being relevant to a meaningful use decision regarding one or more of medications, allergies, immunizations, and problems, wherein generating the inferences comprises:
      applying a forecasting model to the discrete data items, the forecasting model being specific to one of medications, allergies, immunizations, or problems; and
      based on applying the forecasting model to the discrete data items, generating a reconciliation recommendation to reconcile two or more of the electronic records, wherein the reconciliation recommendation is specific to one of medications, allergies, immunizations, or problems.

9. The method of claim 8, wherein prior to reconciling the electronic records obtained from the plurality of diverse systems with one another using an ontology-based model within the knowledge model, the method comprises:
   refactoring the knowledge model by replacing two or more rules with a replacement rule;
   generating at least one axiom based on refactoring the knowledge model; and
   modifying the ontology-based model by adding the at least one axiom to the ontology-based model within the knowledge model.

10. A computerized method comprising:
obtaining electronic records from a plurality of diverse systems, the plurality of diverse record systems having the electronic records in different data formats;
reconciling the electronic records obtained from the plurality of diverse systems with one another using an ontology-based model by:
identifying, in the electronic records obtained from the plurality of diverse systems, information related to one or more of a medications ontology model, an allergies ontology model, an immunizations ontology model, and a problems ontology model;
applying one or more of the medications ontology model, the allergies ontology model, the immunizations ontology model, and the problems ontology model to the electronic records obtained from the plurality of diverse systems; and
based on the application of one or more of the medications ontology model, the allergies ontology model, the immunizations ontology model, and the problems ontology model to the electronic records, recognizing discrete data items that are relevant to a meaningful use decision regarding one or more of medications, allergies, immunizations, and problems; and
generating inferential knowledge based on the discrete data items recognized as being relevant to a meaningful use decision regarding one or more of medications, allergies, immunizations, and problems, wherein the generating comprises:
applying a forecasting model to the discrete data items, the forecasting model being specific to one of medications, allergies, immunizations, or problems; and
based on applying the forecasting model to the discrete data items, generating a reconciliation recommendation to reconcile two or more of the electronic records, the reconciliation recommendation being specific to one of medications, allergies, immunizations, or problems, wherein the recommendation requests a user input to confirm.

11. The method of claim 10, wherein prior to reconciling the electronic records obtained from the plurality of diverse systems with one another using an ontology-based model within the knowledge model, the method comprises:
refactoring the knowledge model by replacing two or more rules with a replacement rule;
generating at least one axiom based on refactoring the knowledge model; and
modifying the ontology-based model by adding the at least one axiom to the ontology-based model within the knowledge model.

* * * * *